United States Patent [19]

Babej et al.

[11] 3,984,459

[45] Oct. 5, 1976

[54] NOVEL CYCLOPENTANE DERIVATIVES

[75] Inventors: Milos Babej, Frankfurt am Main; Wilhelm Bartmann, Neuenhain, Taunus; Gerhard Beck, Frankfurt am Main; Ulrich Lerch, Hofheim, Taunus, all of Germany

[73] Assignee: Hoechst Aktiengesellschaft, Frankfurt am Main, Germany

[22] Filed: June 17, 1974

[21] Appl. No.: 480,319

[30] Foreign Application Priority Data

June 19, 1973 Germany............................ 2331081

[52] U.S. Cl. .................... 260/468 D; 260/240 R; 260/247.2 R; 260/268 R; 260/293.65; 260/347.3; 260/347.4; 260/347.5; 260/410; 260/465.4; 260/468 K; 260/473 G; 260/485 R; 260/487; 260/488 R; 260/501.1; 260/501.11; 260/514 D; 260/514 K; 260/520 C; 260/520 R; 424/285; 424/305; 424/308; 424/317

[51] Int. Cl.² ........................................ C07C 177/00
[58] Field of Search .................... 260/468 D, 514 D

[56] References Cited

UNITED STATES PATENTS

| 3,849,474 | 11/1974 | Abraham et al. | 260/468 |
| 3,868,402 | 2/1975 | Martel et al. | 260/468 |

*Primary Examiner*—Robert Gerstl
*Attorney, Agent, or Firm*—Curtis, Morris & Safford

[57] ABSTRACT

The present invention relates to novel not naturally occurring 10,11-dihydro-derivatives of prostaglandins of the A-series as well as a process for their preparation. The compounds of the invention have an anti-prostaglandin effect and may be used as medicaments for the inhibition or suppression pharmacological properties of the prostaglandins.

8 Claims, No Drawings

NOVEL CYCLOPENTANE DERIVATIVES

Prostaglandins are a group of natural substances which were isolated from different animal tissues. In mammals they are responsible for a great number of pharmacological actions, among which there may be mentioned for example the influence on the contractions of the unstriped musculature and of the blood pressure. Further pharmacological properties are described i.a. in M. F. Cuthbert "The Prostaglandins", Pharmacological and Therapeutic Advances, William Heinemann Medical Books LTD London 1973.

The present invention relates to novel cyclopentane derivatives related to the natural prostaglandins and corresponding to the general formula I

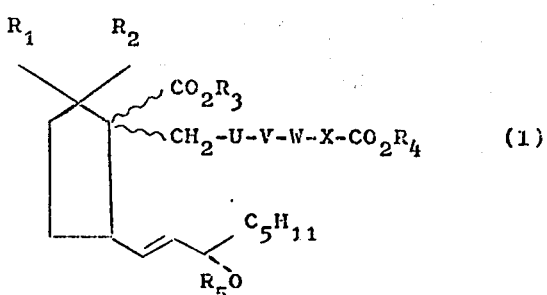

wherein the symbols have the following meaning:

$R_1$ and $R_2$ together represent oxygen or each of the symbols represents hydrogen or hydroxy, $R_1$ and $R_2$ being different, $R_3$ is alkyl having 1 to 5 carbon atoms, $R_4$ is hydrogen, alkyl having 1 to 5 carbon atoms or a physiologically acceptable mono- or polyvalent cation, $R_5$ is hydrogen, an optionally branched, saturated or unsaturated aliphatic hydrocarbon radical or an araliphatic alkyl radical each radical having 1 to 8 carbon atoms, wherein a —CH$_2$— group may be substituted by oxygen, sulfur or carbonyl, an alkyl radical having 1 to 5 carbon atoms, which is substituted by the cyano group or by low-molecular alkoxycarbonyl, a cycloalkyl radical having 5 to 8 carbon atoms, wherein the —CH$_2$— group in 2-position is substituted by an oxygen or sulfur atom, or an aliphatic, cycloaliphatic, aromatic or araliphatic acyl radical having up to 20 carbon atoms, U is a (CH$_2$)$_m$-group, $m$ being 0 to 5, a

group whereby $R_6$ and $R_7$ are identical or different and represent hydrogen or alkyl having 1 to 5 carbon atoms, or a

group wherein $R_6$ and $R_7$ are identical or different and represent hydrogen or alkyl having 1 to 5 carbon atoms, but both cannot simultaneously be hydrogen, if V and W are oxygen and X is (CH$_2$)$_3$, V is a simple bond, oxygen or a radical of the formulae

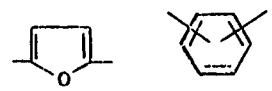

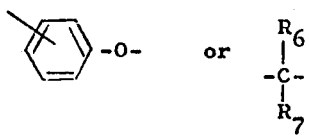

wherein $R_6$ and $R_7$ are identical or different and represent hydrogen or alkyl having 1 to 5 carbon atoms, W is a simple bond or a radical of the formula

wherein $R_8$ and $R_9$ are identical or different and represent hydrogen or alkyl having 1 to 5 carbon atoms, X is a (CH$_2$)$_m$—group, wherein $m$ is 0 to 5.

The invention further relates to a process for the preparation of the cyclopentane derivatives of the general formula I as well as to pharmaceutical compositions which contain these derivatives as active ingredient.

The process comprises a. reacting compounds of the general formula II

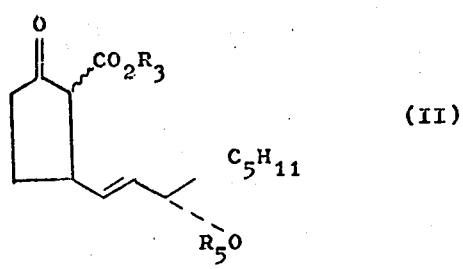

wherein $R_3$ is as defined above, $R_5$ is cycloalkyl, having 5 – 8 C-atoms — a $CH_2$—group in 2-position being substituted by an oxygen or sulfur atom -, in an aprotic solvent in the presence of bases with a halogenated carboxylic acid ester of the general formula III, wherein Hal represents halogen, preferably iodine or bromine and U, V, W, X and $R_4$ are as defined above

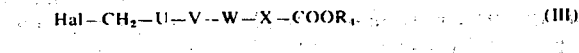

to form compounds of the formula Ia

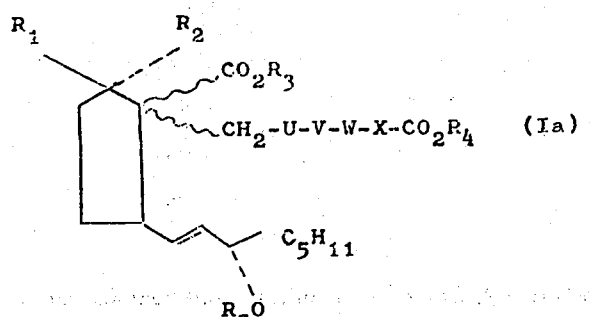

wherein U, V, W and X have the above meaning and $R_1$ and $R_2$ represent oxygen $R_3$ and $R_4$ are alkyl having 1 to 5 carbon atoms and $R_5$ is defined as in formula II, and solvolyzing the reaction products, if desired in the presence of an organic acid to compounds of the formula Ib

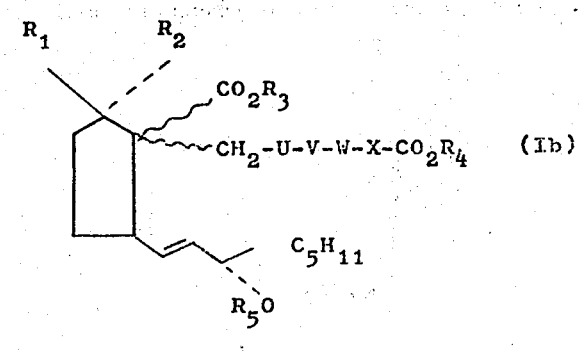

wherein U, V, W and X are as defined above and $R_1$ and $R_2$ represent oxygen, $R_3$ and $R_4$ are alkyl having 1 to 5 carbon atoms and $R_5$ is hydrogen, or b. reacting compounds of the formula Ib with an alkylating or acylating agent to give compounds of the formula Ic

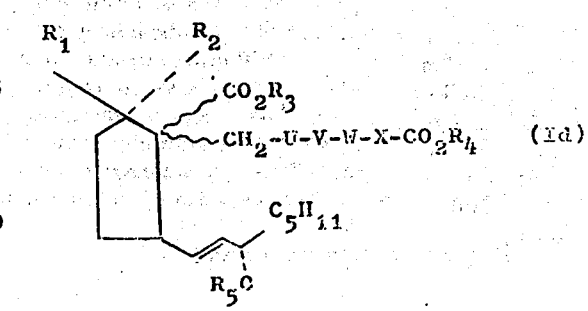

wherein U, V, W and X are as defined above, and $R_1$ and $R_2$ represent oxygen, $R_3$ and $R_4$ are alkyl having 1 to 5 carbon atoms and $R_5$ has the meaning indicated in formula I, or c. reducing compounds of the formulae Ia, Ib and Ic with a complex metal hydride to compounds of the formula Id wherein $R_3$, $R_5$, U, V, W and X have the above meaning and $R_1$ and $R_2$ represent hydrogen or hydroxy and $R_4$ is alkyl having 1 to 5 carbon atoms, or d. saponifying compounds of the formula Id partially in an alkaline medium to compounds of the formula Ie

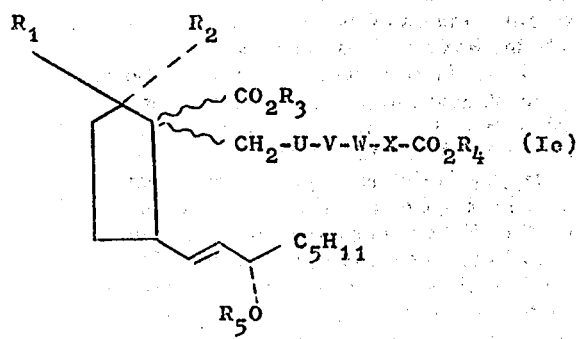

wherein $R_3$, $R_5$, U, V, W and X are as defined above, and $R_1$ and $R_2$ represent hydrogen or hydroxy and $R_4$ is hydrogen or a mono- or polyvalent physiologically acceptable cation, and converting the salts thus obtained, if desired, into the free acid or into other salts.

The reaction of compounds of the formula II with compounds of the formula III occurs according to known methods, expediently at temperatures between room temperature and 140°C in an inert atmosphere. It is particularly suitable to prepare them in the following way:

Compounds of the formula II, as they can be obtained according to Belgian Patent Specification No. 766,521, for example the 5(RS,3'SR)-2-oxo-5[3'-(2''-tetrahydropyranyloxy)-trans-1'-octenyl]-cyclopentane-carboxylic acid ethyl ester, are dissolved in an absolutely dry, aprotic solvent, preferably benzene, toluene or xylene, and 1 to 1.5 mols of an anhydrous base, preferably sodium ethylate or potassium-tert.-butylate, are added, and the whole is stirred for 30 minutes up to 3 hours in an inert gas atmosphere at room temperature.

1 to 2 Mols of a halogenated carboxylic acid ester of the formula III are added, and the mixture is stirred at temperatures between 20° and 140°C — depending on the reactivity of the halogen compound used — between one and 20 hours with exclusion of oxygen (see also Belgian Pat. Specification No. 766,521).

The mixture is subsequently worked up in usual manner and the compounds mostly obtained as oil are purified by chromatography.

As halogenated carboxylic acid esters of the formula III there may be mentioned for example:

7-Iodo-heptanoic acid ethyl ester
7-Iodo-2-methyl heptanoic acid ethyl ester
7-Iodo-3-methyl heptanoic acid ethyl ester
7-Iodo-4-methyl heptanoic acid ethyl ester
7-Iodo-5-methyl heptanoic acid ethyl ester
7-Iodo-6-methyl heptanoic acid ethyl ester
7-Iodo-2-ethyl heptanoic acid ethyl ester
7-Iodo-2-n-butyl heptanoic acid ethyl ester
6-Iodo-hexanoic acid ethyl ester
6-Iodo-2-methyl hexanoic acid ethyl ester
6-Iodo-2-n-butyl hexanoic acid ethyl ester
6-Iodo-2-ethyl hexanoic acid ethyl ester
5-Iodo-pentanoic acid ethyl ester
5-Iodo-2-methyl-pentanoic acid ethyl ester
5-Iodo-2-ethylpentanoic acid ethyl ester
4-Iodo-3-methylbutanoic acid ethyl ester
8-Iodo-octanoic acid
4-Bromo-crotonoic acid ethyl ester
4-Bromo-3-methylcrotonic acid methyl ester
7-Iodo-3-oxa-heptanoic acid methyl ester
7-Iodo-3-oxa-heptanoic acid ethyl ester
7-Iodo-2-methyl-3-oxa-heptanoic acid ethyl ester
7-Iodo-3-methyl-4-oxaheptanoic acid ethyl ester
7-Bromo-3-oxa-cis-5-heptanoic acid methyl ester
7-Bromo-3-oxa-trans-5-heptanoic acid methyl ester
6-Iodo-3-oxa-hexanoic acid ethyl ester
5-Iodo-3-oxa-pentanoic acid methyl ester
8-Bromo-4-oxa-cis-6-octenoic acid methyl ester
7-Iodo-5,5-dimethyl-heptanoic acid ethyl ester
7-Iodo-6,6-dimethyl-3-methyl-2,4-heptadienic acid ethyl ester
5-Bromo-methyl-2-furancarboxylic acid ethyl ester
4-(3-iodopropyl)-benzoic acid ethyl ester
3-(3-iodopropyl)-benzoic acid ethyl ester
2-(3-iodopropyl)-benzoic acid ethyl ester
2-(4-iodobutyl)-benzoic acid ethyl ester
4-Bromomethyl-hydrocinnamic acid ethyl ester
3-Bromomethyl-hydrocinnamic acid ethyl ester
2-Bromomethyl-hydrocinnamic acid ethyl ester
4-(3-Bromomethylphenyl)-butyric acid ethyl ester
4-(2-Bromomethylphenyl)-butyric acid ethyl ester
4-(2-Iodoethoxy)-benzoic acid ethyl ester
4-(3-Iodopropoxy)-benzoic acid ethyl ester
3-(2-Iodoethoxy)-benzoic acid ethyl ester
2-(3-Iodopropoxy)-benzoic acid ethyl ester
4-Bromomethyl-benzoic acid ethyl ester The esters of the invention having the formula Ia are oils which can be used directly or after chromatographic purification for example on silica gel, or for the further reactions.

The existence of a free hydroxyl group ($R_5$ = hydrogen, for example formula Ib) or of a suitable ester or ether (formula Ia, Ic, Id) may be an advantage for the pharmacological application of the compounds of the invention.

Compounds of the formula Ib are obtained by converting compounds of the formula Ia, wherein $R_5$ represents cycloalkyl, preferably a cycloalkyl wherein a —$CH_2$—group is substituted by oxygen such as the tetrahydropyranyl radical, by mild solvolysis, for example in an absolute alcohol, preferably methanol or ethanol with acid catalysts such as p-toluene-sulfonic acid or an organic mono- or polybasic carboxylic acid at temperatures between 0° and 60°C, into the free alcohol (Ib).

Esters or ethers of the formula Ic are prepared in known manner by acylation, alkylation or arylation of the free alcohols of the formula Ib. A suitable acylating agent is for example the aceto-anhydride in the presence of a tertiary base such as pyridine or cyclopentyl-propionyl chloride in the presence of triethyl amine. Ethers of the formula Ic are obtained in known manner by reacting the alcohol of the formula Ib with one of the usual alkylating or arylating agents such as methyl iodide or bromo-acetic acid ethyl ester or 2,4-dinitro-fluorobenzene in aprotic solvents in the presence of a base such as for example potassium carbonate.

Compounds of the formula Id are prepared in known manner by reduction with a complex metal hydride, expediently a metal boranate, preferably alkali boranate, as for example sodium-borohydride or zinc borohydride in an etheric or alcoholic solution, preferably in a solution of an absolute alcohol. The reaction may be carried out at temperatures between —10° and +60°C; generally, a temperature range between 0° and 10°C has proved suitable.

Surprisingly, semiesters of the formula Ie may be obtained from the esters of the formula Id, if the esters of the formula Id are saponified in an aqueous-alcoholic solution at temperatures between 0° and 60°C, preferably at room temperature, with one of the usual bases, for example sodium hydroxide solution. In this process only the ester group with the radical $R_4$ of the general formula Id is converted into the corresponding salt or after a suitable working up into the corresponding acid or into another salt (formula Ie).

The substituent $R_3$ preferably represents a methyl or ethyl group. Among the meanings mentioned for the substituent $R_4$, hydrogen, ethyl as well as among the cations alkali metal and alkaline earth metal cations are preferred. For the formation of salts are furthermore suitable for example organic bases such as benzyl amine, morpholine, piperidine, piperazine or aminocarboxylic acid esters such as glutamic acid diethyl esters.

The radicals particularly preferred for $R_5$ are hydrogen as well as the tetrahydropyranylic radical. Further preferred radicals are: the methyl, ethyl, propyl, butyl, heptyl, octyl, allyl, propargyl, benzyl, methoxymethyl, thiomethoxymethyl, 1-methoxyethyl, 1-methyl-1-methoxyethyl, acetonyl, 3-oxobutyl and the phenacyl radical, furthermore the cyanomethyl, cyanoethyl, 2-cyanopropyl, ethoxycarbonylmethyl as well as the methoxycarbonylethyl radical and finally the acetyl, octamoyl, succinoyl, 2-carboxy-benzoyl radical and the cyclopentyl-propylcarbonyl radical.

U preferably represents a polymethylene chain having up to three CH$_2$-groups. Among the other radicals mentioned for U those are preferred in which $R_6$ or $R_7$ represents an alkyl radical having up to three carbon atoms. The members X, W and V together preferably represent an optionally branched chain having up to 10 members. If V represents a phenylene or phenoxy radical the other radicals U and W may be in a o-, m- or p-position to each other.

The compounds of the invention of the general formula I may be stereoisomers with regard to the position 8 and 12 for $R_1$ and $R_2$ together representing oxygen, and they may be stereoisomers with regard to the position 8, 9 and 12 for $R_1$ and $R_2$ representing H or OH. The compounds of the invention may be applied in the form of their mixtures of isomers, or one or more isomers may be enriched with the aid of usual separating processes such as thin layer or column chromatography or isolated in pure form, as described in detailed form in Example 2.

Apart from the compounds mentioned in the Examples the following compounds may be prepared according to the process of the invention.

(5 RS, 3''SR)-1-(6'-Ethoxycarbonylhexyl)-2-oxo-5-[3''-(2''''-tetra-hydropyranyloxy)-trans-1''-octenyl]-cyclopentane-carboxylic acid-n-butyl ester (5 RS, 3'' SR)-1-(6'-Ethoxycarbonylhexyl)-2-hydroxy-5-[3''-(2''''-tetrahydropyranyloxy)-trans-1''-octenyl]-cyclopentane-carboxylic acid methyl ester (5 RS, 3'' SR)-1-(6'-Isobutyloxycarbonylhexyl)-2-oxo-5-[3''-(2''''-tetrahydropyranyloxy)-trans-1''-octenyl]-cyclopentane-carboxylic acid ethyl ester (5 RS, 3'' SR)-1-(6'-n-Pentyloxycarbonylhexyl)-2-hydroxy-5-(3''-hydroxy-trans-1''-octenyl)-cyclopentane-carboxylic acid ethyl ester (5 RS, 3'' SR)-1-(6'-Methoxycarbonyl-5'-oxahexyl)-2-hydroxy-5-[3''-methoxy-trans-1''-octenyl]-cyclopentane-carboxylic acid ethyl ester (5 RS, 3'' SR)-1-(6'-Ethoxycarbonylhexyl)-2-oxo-5-(3''-cyanmethyloxy-trans-1''-octenyl)-cyclopentanecarboxylic acid ethyl ester (5 RS, 3'' SR)-1-(6'-Ethoxycarbonylhexyl)-2-hydroxy-5-(3''-methoxy-carbonylmethyloxy-trans-1''-octenyl)-cyclopentanecarboxylic acid ethyl ester (5 RS, 3'' SR)-1-(6'-Ethoxycarbonylhexyl)-2-oxo-5-(3''-methoxymethoxy-trans-1''-octenyl)-cyclopentane-carboxylic acid ethyl ester (5 RS, 3'' SR)-1-(6'-Ethoxycarbonylhexyl)-2-oxo-5-[3''-(2''''-methoxy-prop-2''''-oxy)-trans-1''-octenyl]-cyclopentanecarboxylic acid ethyl ester (5 RS, 3'' SR)-1-(6'-Ethoxycarbonylhexyl)-2-hydroxy-5-[3''-(2''',4'''-difluorphenoxy)-trans-1''-octenyl]-cyclopentanecarboxylic acid ethyl ester (5 RS, 3'' SR)-1-(6'-Carboxy-2-methyl-trans-2'-hexenyl)-2-hydroxy-5-[3''-(2''''-tetrahydropyranyloxy)-trans-1''-octenyl]-cyclopentane-carboxylic acid ethyl ester (5 RS, 3'' SR)-1-(6'-Methoxycarbonylhexyl)-2-oxo-5-(3''n-pentyl-carbonyloxy-trans-1''-otenyl)-cyclopentane-carboxylic acid ethyl ester (5 RS, 3'' SR)-1-(6'-Ethoxycarbonylhexyl)-2-hydroxy-5(3''-n-hepta-decanylcarbonyloxy-trans-1''-octenyl)-cyclopentane-carboxylic acid ethyl ester It is surprising that the compounds of the formula I which are closely related to the natural prostaglandins with regard to their structure, as it has been mentioned above, have a strong anti-prostaglandin effect. If, for example, a solution of the compounds of the invention in water is added to the isolated guinea pig ileum or uterus and if for example prostaglandin $E_2$ or $F_2\alpha$ is added to this solution, in concentrations which normally stimulate the isolated ileum or the isolated uterus to strong contractions, only a weaker or no spasmogenic effect of the prostaglandins $E_2$ and $F_2\alpha$ can be detected — depending on the concentrations used. The antiprostaglandin effect of the compounds of the invention could be demonstrated with the aid of the following test arrangement:

As test animals were used brown guinea pigs, males and females having a weight of from about 300 to 400 g. The animals were killed by a blow into the neck, the terminal ileum was rapidly taken off and put into a Petri dish containing a pre-heated Tyrode's solution. The intestine was decomposed into four equal sections (2 to 3 cm). Then the individual sections were put into an organ liquor filled with a Tyrode's solution and bubbled through by oxygen and they were fixed. The bath temperature was 37°C. Composition of the Tyrode's solution: 0.8 g of NaCl, 0.2 g of KCl, 0.55 g of $CaCl_2$, 0.2 g of Mg $Cl_2$, 1.0 g of glucose, 1.0 g of $NaHCO_3$ in 1000 ml of distilled water. The free end was connected with the writing lever by a thread. The charge of the thread was 1 g. After a 30 minutes' recovery time the test itself was initiated. The test consisted in a pre-treatment with the antagonist to be tested and in the administration of the agonist three minutes later. The resulting contraction was compared with the initial contraction achieved by the administration of the agonist only. This latter contraction was considered as being 100 %, and the contraction determined by the compound of the invention acting as antagonist was expressed in percent with regard to this basic contraction. All substances were dissolved in absolute alcohol and further diluted to their final concentrations with phosphate buffer (pH 7.4). As agonists were used prostaglandin $E_2$ (UPJOHN) in the isolated ileum, and $PFG_2$ in the isolated uterus.

The average concentration was determined by means of the probit analysis. The straight line resulting from this method allowed to read the average inhibiting concentration (Table I).

The test arrangement at the isolated uterus differs from the above-described only by the use of the deJalon solution as nutrient solution (composition: 9.0 NaCl, 1.0 g of $NaHCO_3$, 0.45 g of KCl, 0.06 g of $CaCl_2$, Glucose: 1.0 g in 1000 ml of distilled water) (Table I).

Prostaglandin antagonists the structure of which is related to the natural prostaglandins have hitherto been described only by J. Fried in "Prostaglandins", Annals of the New York Academy of Sciences, Vol. 180, April 1971. However, with regard to the process of preparation and the structure of the compounds, the novel compounds are clearly different from the compounds mentioned.

In the literature certain diseases have already been attributed to an increased level of natural prostaglandins. Prostaglandins play their part in inflammable painful and feverish processes (cf. for example J. R. Vane "Inhibition of Prostaglandinbiosynthesis as the Mechanism of Action of Aspirinlike Drugs" in "Advance in the Bioscience" 9, International Conference on Prostaglandins, Pergamon Press Vieweg, 1973).

Furthermore, the pathological spasm of the unstriped musculature may cause for example disturbances of the gastric and intestinal motility and circulatory diseases (cf. for example E. W. Horton et al., Lancet I, page 648, (1969) and Nakanoj, Proc. Soc. Ex. Biol. Med., volume 127, page 1160 (1968)).

Prostaglandins participate in the regulation of the reproductive processes in mammals (cf. for example J. A. MaCracken et al., Nature New Biology, volume 238, page 129 (1972)).

For this reason the compounds of the invention can be used as a medicament due to their anti-prostaglandin effect. Particularly the inhibition or suppression of one or more of the numerous pharmacological properties of the prostaglandins — for example of the spasmogenic effect on certain unstriped muscles — is desired to a large extent.

Therefore, the compounds of the invention may be used for example as a medicament in the case of dysmenorrhea, imminent abortion, glaucoma, osteoporosis and states of shock. They are also active as ovulation inhibitors.

The compounds of the invention of the general formula I may be used in the form of their aqueous solutions or suspensions or as solutions in pharmacologically compatible organic solvents such as for example mono- or polyhydric alcohols, dimethylsulfoxide or dimethylformamide, also in the presence of pharmacologically compatible polymer carriers, as for example polyvinyl pyrrolidone. As preparations are used beside the usual galenic infusion or injection solutions: oral administration forms such as tablets, dragees or gelatin capsules, for which the usual pharmaceutical carriers such as starch, lactose, tragacanth and magnesium carbonate may be used with addition of other suitable substances such as magnesium stearate. The daily dosis used is about 5 mg to 500 mg, preferably 5 to 100 mg.

A dosage unit form preferably contains 5 mg to 50 mg of a compound of the invention.

Suitable preparation for therapeutical purposes are also preparations with local application such as cremes, emulsions, suppositories or aerosols.

The compounds of the invention may be applied individually or together with other pharmacological active substances such as prostaglandin synthethase inhibitors, for example the sodium salt of the acetylsalicylic acid, Furthermore, the compounds described above represent valuable intermediates for the synthesis of novel prostaglandins.

TABLE I

Inhibition of the $PGE_2$- and $PGF_{2\alpha}$ -contraction in the isolated guinea pig ileum or uterus

| Composition according to Example No. | $PGE_2$ 200 ng/ml of $IC_{50}$ ug/ml |
|---|---|
| 4 | 1,2 |
| 8 | < 10 (80 %) |
| 10 | > 10 (10 %) *) |
| 11 | < 10 (80 %) |
| 13 | ~ 5 |
| 30 | < 5 (80 %) |
| 32 | ~ 5 |
| 35 | 2,3 |
| 36 | 4,6 |
| 37 | < 10 (65 %) |
| 44 | < 10 (40 %) |
| 45 | ~ 10 |
| 46 | < 10 (80 %) |

| | $PGF_{2\alpha}$ 40 ng/ml $IC_{50}$ ug/ml |
|---|---|
| 3 | 2 |
| 5 | 10 |

*) in brackets: inhibition in percent for the corresponding dosis

The following Examples illustrate the invention.

EXAMPLE 1

(5 RS, 3″ SR)-1-(6′-Ethoxycarbonylhexyl)-2-oxo-5-[3″-(2‴-tetrahydropyranyloxy)-trans-1″-octenyl]-cyclopentane-carboxylic acid ethyl ester 3.66 g (10 mmols) of (5 RS, 3′ SR)-2-Oxo-5[3′-(2″-tetrahydro-pyranyloxy)-trans-1′-octenyl]-cyclopentan-carboxylic acid ethyl ester were stirred for 1 hour under argon in 30 ml of toluene at room temperature with 1.35 g (12 mmols) of potassium-tert.-butylate and after addition of 4 g (14 mmols) of 7-iodo-heptanoic acid ethyl ester, heated for 14 hours to 110°C. After this time a sample of the solution with an iron-III-chloride solution did not show any enol reaction. The reaction mixture was diluted with 200 ml of diethyl ether, washed with 25 ml of a 25 % sodium dihydrogen-phosphate solution and water, dried over sodium sulfate and the solvent was distilled off in vacuo. 6.2 g of an oily residue were obtained which was chromatographed on 200 g of silica gel (Merck, 70–230 mesh ASTM). The substance was eluated with 1 l of a mixture of solvents of 95 parts of cyclohexane and 5 parts of acetic acid ethyl ester and subsequently with 1 l of a mixture of solvents of 90 parts of cyclohexane and 10 parts of acetic acid ethyl ester and divided into 500 fractions on the whole by means of a fraction collector. The fractions 209 to 280 contained 3.04 g of the substance desired. Thin layer chromatogramm on silica gel plates (Merck):

$R_F$ = 0.28 (cyclohexane/ether 1:1)

N.M.R. multiplet: 5.4 – 5.7 ppm 4.6 – 4.7 ppm 4 – 4.2 ppm.

EXAMPLE 2

(5 RS, 3″ SR)-1-(6′-Ethoxycarbonylhexyl)-2-hydroxy-5-[3″-(2‴-tetrahydropyranyloxy)-trans-1″-octenyl]-cyclopentane-carboxylic acid ethyl ester 450 mg of 5(RS),3″(SR)-1-(6′-Ethoxycarbonylhexyl)-2-oxo-5-[3″-(2‴-tetrahydropyranyloxy)-trans-1″-octenyl]-cyclo,pentane-carboxylic acid ethyl ester were dissolved in 20 ml of absolute ethanol and at 0°C, 100 mg of a solid sodium borhydride were added twice with an interval of 30 minutes. After another hour the preparation was divided. The half B is treated in Example 3. The half A: The solution was mixed at 0°C with glacial acetic acid up to pH 7, the ethanol was evaporated under reduced pressure, the residue was extracted with a small amount of water and a large amount of diethyl ether, the ether layer was washed with water, dried over sodium sulfate and the diethyl ether was distilled off in vacuo. The remaining oil was chromatographed on silica gel (Merck, (70–230 mesh ASTM); Height of the column filling 15 cm, diameter 1.8 cm.

The eluents were the following mixtures of solvents: Cyclohexane/ethyl acetate

| | | | |
|---|---|---|---|
| 250 ml | 95 | to | 5 |
| 100 ml | 92.5 | to | 7.5 |
| 100 ml | 90 | to | 10 |
| 150 ml | 85 | to | 15 |
| 200 ml | 80 | to | 20 |

The substance was decomposed into 200 fractions on the whole with the aid of a fraction collector: the fractions 71 – 101 contained 101 mg of an oil, which produced a uniform spot ($R_F$ = 0.19, eluent:cyclohexane/ether 1:1) in thin layer chromatography on silica gel (coloring by spraying with a 15% phosphonolybdate solution and heating for three minutes to 120°C).

The fractions 101 to 170 additionally contained 111 mg of oil which provided the same N.M.R. spectrum as the fractions 71 to 101 and they partly moved somewhat more slowly in the thin layer chromatogramm.

Total yield: 212 mg

N.M.R. = Multiplets 5.4–5.7 ppm 4.6–4.7 ppm 4–4.3 ppm

EXAMPLE 3

(5 RS, 3″ SR)-1-(6′-carboxyhexyl)-2-hydroxy-5-(3″-hydroxy-trans-1″-octenyl)-cyclopentane-carboxylic acid ethyl ester The half of the preparation mixture of Example 2 was stirred with 0.6 ml of 1N NaOH at room temperature, then the reaction solution was evaporated under reduced pressure, mixed with saturated sodium chloride solution and acidified with a 2N hydrochloric acid to pH 1 to 2. The mixture was extracted twice with 200 ml of diethyl ether, the combined ether extracts were washed with water, dried and evaporated. 180 mg of oil were obtained which were dissolved in 5 ml of ethanol and stirred with 4 ml of a 2% oxalic acid solution for 6 hours at room temperature. The ethanol was distilled off at reduced pressure, the remaining aqueous solution was mixed with saturated sodium chloride solution and extracted twice with 200 ml of diethyl ether in each case. The ether solution was washed until neutral, dried and evaporated. 155 mg of a clear oil were obtained which were chromatographed on $SiO_2$. Height of the column filling 14 cm, diameter of the column: 1.8 cm.

The eluation was carried out with the following mixtures of solvents and 320 fractions on the whole were taken off: Cyclohexane/ethyl acetate with 1% of glacial acetic ester in each case

| | | | | |
|---|---|---|---|---|
| 200 ml of | 92.5 | to | 7.5 | |
| 200 ml of | 90 | to | 10 | |
| 200 ml of | 80 | to | 20 | after evaporating these fractions |
| 200 ml of | 70 | to | 30 | 84 mg of the product were obtained. |

$R_F = 0.19$ (cyclohexane/ethyl acetate/glacial acetic acid 40:60:1)

N.M.R. multiplet 5.4 – 5.7 ppm singulet 5.3 ppm

EXAMPLE 4

(5 RS, 3″ SR)-1-(6′-Ethoxycarbonyl-3′-methylhexyl)-2-oxo-5-[3″-(2‴-tetrahydropyranyloxy)-trans-1″-octenyl]-cyclo-pentane-carboxylic acid ethyl ester a. (5-Bromo-3-methylpentyl)-malonic acid diethyl ester 15 g (0.5 mol) of a 80% suspension of sodium hydride in mineral oil were added portionwise to 88 g (0.55 mol) of malonic ester in 200 ml of absolute toluene and 50 ml of dimethylformamide, while stirring and with exclusion of humidity. Until the development of hydrogen was finished the mixture was heated to 50°C and then 125 g (0.51 mol) of 1,5-dibromo-3-methyl-pentane (JACS 85, 3604 (1963)) were added.

The reaction mixture was heated to the boil until it had a neutral reaction to phenol phthaline.

After cooling the mixture was washed three times with water and the organic phase was dried, freed from the solvent and distilled off.

Boiling point$_{0.2}$: 120°–121°C b. 7-Bromo-5-methyl-heptanoic acid 30 g of (5-bromo-3-methylpentyl)-malonic acid diethyl ester were heated to the boil, while stirring, with 15 ml of 48% HBr and 15 ml of HBr/glacial acetic acid, whereby the low-boiling products were distilled off. After 7 hours the cooled reaction solution was distributed between benzene and water and the organic phase was evaporated with MgSO$_4$ after drying and distilled off.

Boiling point$_1$: 119°– 121°C c. 7-Bromo-5-methylheptanoic acid ethyl ester 14.0 g of 7-Bromo-5-methylheptanoic acid, 26 ml of absolute ethanol and 1 ml of concentrated H$_2$SO$_4$ were heated to the boil for 10 hours with exclusion of humidity. After cooling the reaction mixture was poured, while stirring and strongly cooling, onto a mixture of 50 ml of ether, 20 ml of water and 6 g of NaHCO$_3$. When the development of CO$_2$ was finished, the organic phase was separated and the aqueous phase was extracted twice with ether. The combined organic phases were washed with a saturated NaHCO-hd 3-solution, dried, evaporated and distilled off.

Boiling point$_{0.65}$: 89° – 90°C

NMR: 4.15 ppm (2 H, quadruplet); 3.46 ppm (2 H triplet); 2.30 ppm (2 H, triplet); 0.92 ppm (3 H, dublet);

d. 7-Iodo-5-methylheptanoic acid ethyl ester 12.3 g of 7-Bromo-5-methylheptanoic acid ethyl ester and 18 g of NaJ were refluxed for 10 hours in 250 ml of acetone. The solvent was eliminated by the rotation evaporator and the residue was distributed between petroleum ether and water. The organic phase was distilled off after drying.

Boiling point$_{0.4}$: 85°–88°C e. (5 RS, 3″ SR)-1-(6′-Ethoxycarbonyl-3′-methyl-hexyl)-2-oxo-5-[3″-(2‴-tetrahydropyranyloxy)-trans-1″-octenyl]-cyclopentane-carboxylic acid ethyl ester 720 mg (6.4 mmols) of sublimated potassium-tert-.butylate were added, while stirring and under an argonate atmosphere, to 2.0 g (5.5 mmols) of (5 RS, 3′ SR)-2-oxo-5-[3′-(2″-tetrahydropyranyloxy)-trans-1′-octenyl]-cyclo-pentane-carboxylic acid ethyl ester in 20 ml of dry toluene, and the mixture was stirred for 20 minutes at room temperature. 3.0 g (10 mmols) of 7-iodo-5-methyl-heptanoic acid ethyl ester were added to the reaction mixture, and the whole was refluxed in an argonate atmosphere, until the analysis by thin layer chromatography (cyclohexane/ether 1:1 on Al$_2$O$_3$-plates) showed the end of the reaction. This occurred after about 9 hours. While cooling strongly, the mixture was adjusted to pH 6 – 7 with a 2N NaH$_2$PO$_4$ - solution, and the reaction mixture was distributed between toluene and water. The organic phase was dried after washing with MgSO$_4$ and evaporated. The remaining yellow oil was chromatographed on 120 g of SiO$_2$ (Merck, 70-230 mesh ASTM) with 2 liters of a mixture of cyclohexane/ethyl acetate 9:1.

The eluate was divided in 180 equal fractions. After the evaporation of the solvent the fractions 59–95 yielded 1.75 g of (5 RS, 3″ SR)-1-(6′-ethoxycarbonyl-3′-methylhexyl)-2-oxo-5-[3″-(2‴-tetrahydropyranyloxy)-trans-1″-octenyl]-cyclopentane-carboxylic acid ethyl ester as a colorless oil.

$R_F = 0.28$ (cyclohexane/ethyl acetate 85:15 on silica gel plates)

NMR: 5.74 – 5.40 ppm (2 H, multiplet); 4.70 ppm (1 H, broad signal); 4.4 – 3.3 ppm (7 H, quadruplet superimposed by multiplet), signal group between 2.5 and 0.7 ppm (42 H).

EXAMPLE 5

(5 RS, 3″ SR)-1-(6′-Carboxy-3′-methylhexyl)-2-hydroxy-5-[3″-(2‴-tetrahydropyranyloxy)-trans-1″-octenyl]-cyclo-pentane-carboxylic acid ethyl ester A solution of 1.02 g (2 mmols) of (5 RS, 3″ SR)-(6′-ethoxy-carbonyl-3′-methylhexyl)-2-oxo-5-[3″-(2‴-tetrahydropyranyloxy)-trans-1″-octenyl]-cyclopentane-carboxylic acid ethyl ester in 25 ml of absolute ethanol was mixed portionwise with 250 mg (6.6 mmols) of dry NaBH$_4$. After stirring for one and a half hours the reduction was finished. 7 ml of a 0.7N sodium hydroxide solution (4.9 mols) were added to the reaction solution and the mixture was stirred for 4 hours at room temperature. The solvent was removed under reduced pressure at a bath temperature of 25°C, ether and water were poured to the residue and while strongly cooling, the whole was adjusted to pH 2 with diluted hydrochloric acid. The aqueous phase was extracted twice with ether, the organic phase was washed with water, dried and the solvent was evaporated. The oily residue was chromatographed on 60 g of SiO$_2$ with a mixture of cyclohexane/acetone 7:3. By this was a colorless viscous oil (520 mg) was obtained.

$R_F = 0.38$ (Cyclohexane/acetone 1:1)

NMR: 5.55 ppm (2 prot.); 4.67 (1 prot.); 4.5 – 3.3 ppm (5 prot.); 2.6 – 0.7 ppm (40 prot.)

EXAMPLE 6

(5 RS, 3″ SR)-1-(6′-Carboxy-3′-methylhexyl)-2-hydroxy-5-(3″-hydroxy-trans-1″-octenyl)-cyclopentane-carboxylic acid ethyl ester 504 mg (1 mmol) of (5 RS, 3″ SR)-1-(6′-Carboxy-3′-methylhexyl)-2-hydroxy-5-[3‴-(2‴-tetrahydropyranyloxy)-trans-1″-octenyl]-cyclopentane-carboxylic acid ethyl ester, 6.5 ml of ethanol and 4.2 ml of a 2% aqueous oxalic acid were heated for 1 hour to 60°C while stirring. The main portion of the solvent was removed under reduced pressure, the residue was distributed between ether and water, the organic phase was washed with water, dried and the solvent was evaporated. In the chromatography on 40 g of $SiO_2$ with a mixture of cyclohexane/ethyl acetate/glacial acetic acid 60:40:1 fractions of 5 ml each were taken off. From the fractions 47 to 65, 251 mg of a colorless oil were obtained.

$R_F = 0.13$ (cyclohexane/ethyl acetate/glacial acetic acid 40:60:1)

NMR: 5.54 ppm (2 prot.); 5.10 ppm (3 prot.); 4.15 – 3.9 ppm (4 prot.); 2.4 – 0.7 ppm (33 prot.)

EXAMPLE 7

(5 RS, 3″ SR)-1-(6′-Ethoxycarbonyl-4′-methylhexyl)-2-oxo-5-[3″-(2‴-tetrahydropyranyloxy)-trans-1″-octenyl]-cyclopentane-carboxylic acid ethyl ester a. 4-Methylpimelic acid dinitrile 127 g (2.6 mols) of dry NaCN in 600 ml of dry dimethylsulfoxide were heated to an inner temperature of 90°C and while stirring and exclusion of humidity, 173 g (1.1 mols) of 1.5-dichloro-3-methylpentane were added dropwise within 15 minutes. The inner temperature was increased to 125°C and maintained at this degree for another 30 minutes. The mixture was cooled and distributed between benzene and water/saturated sodium chloride solution 1:1. The organic phase was washed twice with saturated sodium chloride solution, then dried, evaporated under reduced pressure and the residue was distilled off.

Boiling point$_{0.8}$: 118°– 120°C b. 4-Methylpimelic acid 123 g of 4-Methylpimelic acid dinitrile were heated to the boil for 8 hours with 500 ml of concentrated hydrochloric acid, and the mixture was stirred vigourously. The cooled reaction mixture was saturated with sodium chloride and extracted several times with ether. The combined ether extracts were dried and evaporated; thereby 145 g of crude 4-methylpimelic acid were obtained, which were reacted without any further purification.

c. 4-Methylpimelic acid monoethyl ester 145 g of crude 4-methylpimelic acid, 68 ml of absolute ethanol and 12 ml of concentrated sulfuric acid were refluxed for 5 hours. The mixture was poured onto ice and extracted several times. The combined ether solutions were extracted with saturated $NaHCO_3$ until the development of $CO_2$ was finished. The aqueous extracts were covered with a layer of ether and adjusted while stirring to pH 2 to 3 with diluted sulfuric acid. The ether layer was separated and the aqueous phase was saturated with $(NH_4)_2SO_4$ and extracted three times with ether.

After drying and evaporating the organic phase a colorless oil was obtained, which was distilled off under highly reduced pressure.

Boiling point$_{0.8}$: 133° – 136°C d. 7-Hydroxy-4-methylheptanoic acid ethyl ester Diborane gas was introduced into a solution of 35.4 g (0.175 mol) of 4-methylpimelic acid monoethyl ester in 130 ml of absolute THF; the gas was produced by dropwise addition of a solution of 13.2 g (0.35 mol) of $NaBH_4$ in 270 ml of absolute diethyleneglycol-dimethyl ether to a solution of 52.5 g (0.37 mol) of borotrifluoride etherate in 80 ml of diethylene-glycol-dimethyl ether. Stirring was continued for another 3 hours at room temperature and 50 ml of ethanol were added. The reaction mixture was allowed to stand over night, the solvent was removed at the rotation evaporator and the residue was distributed between ether and a saturated $NaHCO_3$-solution. After drying an oil was obtained during the evaporation of the organic phase which was distilled off under highly reduced pressure.

Boiling point$_{0.2}$: 81° – 84°C e. 7-Bromo-4-methylheptanoic acid ethyl ester 27 g of 7-hydroxy-4-methylheptanoic acid ethyl ester, 50 ml of chloroform and 27 g of phosphor tribromide were stirred for 2 hours at room temperature and stirred for 1 hour at 50°C. At an inner temperature of 5° to 10°C, 50 ml of ethanol were added dropwise while cooling, the volatile constituents were evaporated under reduced pressure and the residue was distilled off.

Boiling point$_{0.2}$: 85° – 87°C f. 7-Iodo-4-methylheptanoic acid ethyl ester

Test in analogy to 4 d).

Boiling point$_{0.3}$: 115° – 120°C

NMR: 4.15 ppm (2 H, quadruplet); 3.20 ppm (2 H, triplet); 2.30 ppm (2 H, triplet); 0.9 ppm (3 H, duplet).

g. (5 RS,3″ SR)-1-(6′-Ethoxycarbonyl-4′-methylhexyl)-2-oxo-5[3″-(2‴-tetrahydropyranyloxy)-trans-1″-octenyl]-cyclopentane-carboxylic acid ethyl ester Test in analogy to 4 e) from (5RS,3′SR)-2-oxo-5-[3′-(2″-tetrahydropyranyloxy)-trans-1′-octenyl]-cyclopentanecarboxylic acid ethyl ester and 7-iodo-4-methylheptanoic acid ethyl ester (reflux temperature: 6 hours)

$R_F = 0.55$ ($SiO_2$ cyclohexane/ethyl acetate 6:4)

The NMR spectrum was practically identical to that of the product of test 4 e).

EXAMPLE 8

(5RS,3″SR)-1-(6′-Carboxy-4′-methylhexyl)-2-hydroxy-5-[3″-(2‴-tetrahydropyranyloxy)-trans-1″-octenyl]-cyclopentane-carboxylic acid ethyl ester Test in analogy to Example 5 from (5RS,3″SR)-1-(6′-ethoxy-carbonyl-4′-methylhexyl)-2-oxo-5-[3″-(2‴-tetrahydropyranyloxy)-trans-1″-octenyl]-cyclopentane-carboxylic acid ethyl ester $R_F = 0.29$ (Cyclohexane/ethyl acetate/glacial acetic acid 40:60:1)

$R_F = 0.31$ (Cyclohexane/acetone 6:4)

The NMR spectrum practically did not differ from the spectrum described in Example 5.

EXAMPLE 9

(5RS,3''SR)-1-(6'-Carboxy-4'-methylhexyl)-2-hydroxy-5-[3''-hydroxy-trans-1''-octenyl]-cyclopentane-carboxylic acid ethyl ester Test in analogy to Example 6 from (5RS,3''SR)-1-(6'-Carboxy-4'-methylhexyl)-2-hydroxy-5-[3''-(2'''-tetrahydropyranyloxy)-trans-1''-octenyl]-cyclopentane-carboxylic acid ethyl ester $R_F = 0.18$ (Cyclohexane/ethyl acetate/glacial acetic acid 40:60:1)

The NMR spectrum was nearly identical to the spectrum described in Example 6.

EXAMPLE 10

(5RS,3''SR)-1-(6'-Ethoxycarbonyl-5'-methylhexyl)-2-oxo-5-[3''-(2'''-tetrahydropyranyloxy)-trans-1''-octenyl]-cyclopentane-carboxylic acid ethyl ester a. Methyl-(4-phenoxybutyl)-malonic acid diethyl ester After the development of hydrogen was finished 30 g (1 mol) of a 80% suspension of sodium hydride in mineral oil were added portionwise to 191 g (1.1 mols) of methylmalonic acid diethyl ester in 300 ml of absolute toluene and 50 ml of dry dimethylformamide were added and after that, 252 g (1.1 mols) of 4-phenoxy-1-bromobutane (J.O.C. 27, 1290 (1962) were added. The mixture was refluxed for about 13 hours until the medium had a neutral reaction. It was worked up as in 4 a).

Boiling point$_{0.08}$: 137°C b. 2-Methyl-6-phenoxy-hexanoic acid 242 g of methyl-(4-phenoxybutyl)-malonic acid diethyl ester, 1000 ml of a 20% sodium hydroxide solution and 100 ml of ethanol were refluxed for 12 hours.

The ethanol was evaporated under reduced pressure and the aqueous solution was adjusted to an acid range with a 20% sulfuric acid, whereby the dicarboxylic acid was precipitated. After suction-filtering it was dissolved in methylene chloride, washed with water and evaporated and the residue was heated for 5 hours to 185°C. When cooling the product crystallized. It could be recrystallized from cyclohexane.

Melting point: 74.5° – 75.5°C.

c. 1-Hydroxy-2-methyl-6-phenoxy-hexane

A solution of 129 g of 2-methyl-6-phenoxy-hexanoic acid in 200 ml of absolute ether and 100 ml of absolute THF was added dropwise, under exclusion of humidity, to 32 g (0.84 mol) of LiAlH$_4$ in 1.2 l of absolute ether. After reflux and stirring for 5 hours the LiAlH$_4$ in excess was destroyed with acetic acid and then destroyed by dropwise addition of water and a 10% sulfuric acid. The organic layer was washed with saturated NaHCO$_3$-solution, dried and evaporated. The crude product was immediately further reacted.

d. 1-Chloro-2-methyl-6-phenoxy-hexane

A solution of 60 g of thionyl chloride in 50 ml of CHCl$_3$ was added dropwise to 100 g of 1-Hydroxy-2-methyl-6-phenoxy-hexane in 200 ml of CHCl$_3$ and 0.5 ml of DMF. The solution was refluxed until the development of the gas was finished and then poured onto ice. The aqueous phase was extracted twice with CHCl$_3$ and the combined organic phases were washed with water and finally with a saturated NaHCO$_3$-solution, dried with MgSO$_4$, evaporated and the residue was distilled off.

Boiling point$_{0.5}$: 117° – 120°C.

e. 3-Methyl-7-phenoxy-heptanoic acid nitrile 63 g of 1-Chloro-2-methyl-6-phenoxy-hexane were added dropwise within 15 minutes to a mixture heated to 100°C of 17 g of NaCN and 90 ml of dry DMSO. The temperature was increased to 140°C. After 20 minutes the reaction was finished according to the analysis by thin layer chromatography (benzene). The mixture was distributed between water and ether. By drying, evaporating and distilling the organic phase 56.7 g of the chlorine compound having a boiling point$_{0.4}$ of 131° – 134°C were obtained.

f. 7-Bromo-3-methylheptanoic acid 39.2 g of 3-methyl-7-phenoxy-heptanoic acid nitrile were refluxed for 5 hours with 160 ml of a 48% HBr. After distribution between benzene and water, 27.8 g of bromocarboxylic acid having a boiling point$_{0.2}$ of 108° – 110°C were obtained by distilling off the organic phase.

g. 7-Bromo-3-methylheptanoic acid ethyl ester

Test in analogy to 4 c) with 7-bromo-3-methylheptanoic acid.

Boiling point$_{0.1}$: 62° – 65°C h. 7-Iodo-3-methylheptanoic acid ethyl ester

Test in analogy to 4 d) with 7-bromo-3-methylheptanoic acid ethyl ester.

Boiling point$_{0.6}$: 92° – 94°C.

i. (5RS,3''SR)-1-(6'-Ethoxycabonyl-5'-methylhexyl)-2-oxo-5-[3''-(2'''-tetrahydropyranyloxy)-trans-1''-octenyl]-cyclopentane-carboxylic acid ethyl ester Test in analogy to 4 e) from (5RS,3'SR)-2-Oxo-5-[3'-(2''-tetrahydropyranyloxy)-trans-1'-octenyl]-cyclopentane-carboxylic acid ethyl ester and 7-Iodo-3-methyl-heptanoic acid ethyl ester (6 hours, 110°C)

$R_F = 0.61$ (SiO$_2$, Cyclohexane/ethyl acetate 1:1)

The NMR spectrum did not differ very much from the spectrum described in Example 4 e).

EXAMPLE 11

(5RS,3''SR)-1-(6'-Carboxy-5'-methylhexyl)-2-hydroxy-5-[3''-(2'''-tetrahydropyranyloxy)-trans-1''-octenyl]-cyclopentane-carboxylic acid ethyl ester Test in analogy to Example 5 from (5RS,3''SR)-1-(6'-ethoxycarbonyl-5'-methylhexyl)-2-oxo-5-[3''-(2'λ''-tetrahydropyranyloxy)-trans-1''-octenyl]-cyclopentane-carboxylic acid ethyl ester $R_F = 0.29$ (Cyclohexane/ethyl acetate/glacial acetic acid 40:60:1)

The NMR-spectrum was nearly identical to the spectrum described in Example 5.

EXAMPLE 12

(5RS,3''SR)-1-(6'-Carboxy-5'-methylhexyl)-2-hydroxy-5-(3''-hydroxy-trans-1''-octenyl)-cyclopentane-carboxylic acid ethyl ester Test in analogy to Example 6 from (5RS,3''SR)-1-(6'-Carboxy-5'-methylhexyl)-2-hydroxy-5-[3''-(2'''-tetrahydropyranyloxy)-trans-1''-octenyl]-cyclopentane-carboxylic acid ethyl ester $R_F = 0.20$ (Cyclohexane/ethyl acetate/glacial acetic acid 40:60:1)

The NMR-spectrum was nearly identical to the spectrum described in Example 6.

EXAMPLE 13

(5RS,3''SR)-1-(6'-Ethoxycarbonylheptyl)-2-oxo-5-[3''-(2'''-tetrahydropyranyloxy)-trans-1''-octenyl]-cyclopentane-carboxylic acid ethyl ester Test in analogy to 4 e) from (5RS,3'-SR)-2-oxo-5-[3'-(2''-tetrahydropyranyloxy)-trans-1'-octenyl]-cyclopentane-carboxylic acid ethyl ester and 7-iodo-methylheptanoic acid ethyl ester (5 hours; 110°C)

$R_F = 0.51$ (Cyclohexane/ethyl acetate 6:4 on $SiO_2$-plates)

The NMR-spectrum was nearly identical to the spectrum of Example 4 e).

The 7-iodo-2-methylheptanoic acid ethyl ester could be prepared from methylmalonic acid diethyl ester and 1.5-dibromopentane in analogy to the Examples 4(a) to 4(d).

Boiling point$_{0.2}$: 80°C.

NMR: 4.18 ppm (2 H, quadruplet); 3.43 ppm (2 H, triplet); 1.26 ppm (3 H, triplet); 1.14 ppm (3 H, duplet).

EXAMPLE 14

(5RS,3''SR)-1-(6'-Ethoxycarbonyloctyl)-2-oxo-5-[3''-(2'''-tetrahydropyranyloxy)-trans-1''-octenyl]-cyclopentane-carboxylic acid ethyl ester Test in analogy to 4 e) from (5RS,3'SR)-2-Oxo-5-[3'-(2''-tetrahydropyranyloxy)-trans-1'-octenyl]-cyclopentane-carboxylic acid ethyl ester and 2-ethyl-7-iodo-heptanoic acid ethyl ester (6 hours, 100°)

$R_F = 0.30$ (Cyclohexane/ethyl acetate 85:15, silica gel plate).

The NMR-spectrum did not differ very much from the spectrum described in Example 4 e), only in the range of the aliphatic protons.

The 2-ethyl-7-iodo-heptanoic acid ethyl ester was prepared according to Example 4(a) to 4(d) from ethyl malonic acid ester and 1,5-dibromo-pentane.

Boiling point$_{0.4}$: 92° – 94°C.

EXAMPLE 15

(5RS,3''SR)-1-(6'-Ethoxycarbonyldecyl)-2-oxo-5-[3''-(2'''-tetrahydropyranyloxy)-trans-1''-octenyl]-cyclopentane-carboxylic acid ethyl ester Test in analogy to Example 1 from 2.2 g (6 mmols) of (5RS,3'SR)-2-Oxo-5-[3'-(2''-tetrahydropyranyloxy)-trans-1'-octenyl]-cyclopentane-carboxylic acid ethyl ester, 900 mg (8 mmols) of potassium-tert.-butylate and 3.4 g (10 mmols) of 7-iodo-2-n-butylheptanoic acid ethyl ester in 20 ml of toluene (8 hours at 110°C). Chromatography on 100 g of $SiO_2$ yielded 1.8 g of pure product.

$R_F = 0.4$ (cyclohexane/ether 1:1).

The 7-iodo-2-n-butylheptanoic acid ethyl ester was prepared from n-butyl-malonic acid diethyl ester and 1,5-dibromopentane according to the reactions 4(a) to 4(d).

Boiling point$_{0.2}$: 125° – 128°C.

EXAMPLE 16

(5RS,3''SR)-1-(5'-Ethoxycarbonylpentyl)-2-oxo-5-[3''-(2'''-tetrahydropyranyloxy)-trans-1''-octenyl]-cyclopentane-carboxylic acid ethyl ester Test in analogy to 4(a) from (5RS,3'SR)-2-oxo-5-[3'-(2''-tetrahydropyranyloxy)-trans-1'-octenyl]-cyclopentane-carboxylic acid ethyl ester and 6-iodohexanoic acid ethyl ester (reflux temperature 5 hours).

$R_F = 0.23$ (cyclohexane/ethyl acetate 85:15; silica gel plate).

The NMR-spectrum differs from the spectrum of Example 4(e) only in the range of the aliphatic protons.

The 6-iodohexanoic acid ethyl ester was prepared according to the process described in Example 4(a) to 4(d) from 1,4-dibromo-butane and malonic acid diethyl ester.

Boiling point$_{0.15}$: 72° – 73°C.

EXAMPLE 17

(5RS,3''SR)-1-(5'-Ethoxycarbonylhexyl)-2-oxo-5-[3''-(2'''-tetrahydropyranyloxy)-trans-1''-octenyl]-cyclopentane-carboxylic acid ethyl ester Test in analogy to Example 1 from 2.2 g (6 mmols) of (5RS,3'SR)-2-Oxo-5-[3'-(2''-tetrahydropyranyloxy)-trans-1'-octenyl]-cycopentane-carboxylic acid ethyl ester, 900 mg (8 mmols) of potassium-tert.-butylate and 3.26 g (10 mmols) of 6-iodo-2-methyl-hexanoic acid ethyl ester in 30 ml of toluene (6 hours; 110°).

Chromatography on $SiO_2$ (column 25 × 3.2 cm) yielded 2.54 g of a pure compound.

$R_F = 0.50$ (cyclohexane/ether 1:1)

The 6-iodo-2-methylhexanoic acid ethyl ester was obtained in analogy to Example 4(a) to 4(d) from methylmalonic acid diethyl ester and 1,4-dibromo-butane.

Boiling point$_{0.15}$: 74° – 75°C.

EXAMPLE 18

(5RS,3''SR)-1-(5'-Ethoxycarbonylheptyl)-2-oxo-5-[3''-(2'''-tetrahydropyranyloxy)-trans-1''-octenyl]-cyclopentane-carboxylic acid ethyl ester Test in analogy to Example 4(e) from (5RS,3'SR)-2-Oxo-5-[3'-(2''-tetrahydropyranyloxy)-trans-1'-octenyl]-cyclopentane-carboxylic acid ethyl ester and 2-ethyl-6-iodo-hexanoic acid ethyl ester (6.5 hours; reflux temperature).

$R_F = 0.55$ (Cyclohexane/ethyl acetate 6:4)

The NMR-spectrum did not differ very much from the spectrum described in Example 4e).

The 2-ethyl-6-iodo-hexanoic acid ethyl ester required was prepared according to the reactions described in Example 4(a) to 4(d) from ethylmalonic acid diethyl ester and 1,4-dibromobutane.

The 2-ethyl-6-iodo-hexanoic acid ethyl ester boiled at 80° – 82°C and 0.3 mm mercury.

EXAMPLE 19

(5RS,3''SR)-1-(5'-Ethoxycarbonylmethyl)-2-oxo-5-[3''-(2'''-tetrahydropyranyloxy)-trans-1''-octenyl]-cyclopentane-carboxylic acid ethyl ester Test in analogy to Example 1 from 2.2 g (6 mmols) of (5RS,3'SR)-2-Oxo-5-[3'-(2''-tetrahydropyranyloxy)-trans-1'-octenyl]-cyclopentane-carboxylic acid ethyl ester, 900 mg (8 mmols) of potassium-tert.-butylate and 3.26 g (10 mmols) of 6-iodo-2-n-butylhexanoic acid ethyl ester in 30 ml of toluene (6 hours at 110°).

By column chromatography on $SiO_2$ (column with 20.5 × 4.3 cm) 1.9 g of a pure product and 610 mg of a slightly impure product were obtained.

$R_F = 0.45$ (cyclohexane/ether 1:1).

The 6-iodo-2-n-butylhexanoic acid ethyl ester was prepared as described in Example 4(a) to 4(d) from n-butylmalonic acid diethyl ester and 1,4-dibromobutane.

Boiling point$_{0.9}$: 118° – 120°C.

EXAMPLE 20

(5RS,3''SR)-1-(4'-Ethoxycarbonylbutyl)-2-oxo-5-[3'''-(2''''-tetrahydropyranyloxy)-trans-1''-octenyl]-cyclopentane-carboxylic acid ethyl ester Test in analogy to 4(e) from (5RS,3'SR)-2-oxo-5-[3'-(2''-tetrahydropyranyloxy)-trans-1'-octenyl]-cyclopentane-carboxylic acid ethyl ester and 5-iodo-valerianic acid ethyl ester (5 hours, reflux temperature).

$R_F$ = 0.54 (cyclohexane/ethyl acetate 1:1) = 0.23 (cyclohexane/ethyl acetate 85:15)

The 5-iodo-valerianic acid ethyl ester was prepared in analogy to Example 4(d) from 5-bromo-valerianic acid ethyl ester (Helv. 1949, 540; see also JACS 50, 1967 (1928)).

Boiling point$_{0.2}$: 62° – 65°C.

EXAMPLE 21

(5RS,3''SR)-1-(4'-Ethoxycarbonylpentyl)-2-oxo-5-[3''-(2'''-tetrahydropyranyloxy)-trans-1''-octenyl]-cyclopentane-carboxylic acid ethyl ester Test in analogy to 4(e) from (5RS,3'SR)-2-oxo-5-[3'-(2''-tetrahydropyranyloxy)-trans-1'-octenyl]-cyclopentane-carboxylic acid ethyl ester and 5-iodo-2-methylvalerianic acid ethyl ester (6 hours, reflux temperature).

$R_F$ = 0.22 (cyclohexane/ether 1:1, Al$_2$O$_3$).

The 5-iodo-2-methyl-valerianic acid ethyl ester was prepared according to Example 4(a) to 4(d) from methylmalonic acid diethyl ester and 1,3-dibromo-propane.

Boiling point $_{0.5}$: 70° – 71°C.

EXAMPLE 22

(5RS,3''SR)-1-(4'-Ethoxycarbonylhexyl)-2-oxo-5-[3''-(2'''-tetrahydropyranyloxy)-trans-1''-octenyl]-cyclopentane-carboxylic acid ethyl ester Test in analogy to Example 1 from 2.2 g (6 mmols) of (5RS,3'SR)-2-oxo-5-[3'-(2''-tetrahydropyranyloxy)-trans-1'-octenyl]-cyclopentane-carboxylic acid ethyl ester, 900 mg (8 mmols) of potassium-tert.-butylate and 2.84 g (10 mmols) of 2-ethyl-5-iodo-valerianic acid ethyl ester in 20 ml of toluene (7 hours, 110°C). Chromotography on 120 g of SiO$_2$ yielded 2.08 g of the compound desired.

$R_F$ = 0.50 (cyclohexane/ether 1:1)

The 2-ethyl-5-iodo-valerianic acid ethyl ester was prepared according to Example 4(a) to 4(d) from ethylmalonic acid diethyl ester and 1,3-dibromo-propane.

Boiling point$_{0.4}$: 74° – 75°C.

EXAMPLE 23

(5RS,3''SR)-1-(3'-Ethoxycarbonyl-trans-2'-propenyl)-2-oxo-5-[3''-(2'''-tetrahydropyranyloxy)-trans-1''-octenyl]-cyclopentane-carboxylic acid ethyl ester Test in analogy to 4(e) from (5RS,3''SR)-2-Oxo-5-[3'-(2''-tetrahydropyranyloxy)-trans-1'-octenyl]-cyclopentane-carboxylic acid ethyl ester and 4-bromo-crotonic acid ethyl ester. The reaction was finished after 3 hours at 50°C.

$R_F$ = 0.59 (cyclohexane/ethyl acetate 1:1).
NMR: Olefinical protons at 6.6 ppm (1 H, multiplet); 5.4 ppm (1 H, dublet); 5.41 ppm (2 H, multiplet).

EXAMPLE 24

(5RS,3''SR)-1-(3'-Ethoxycarbonyl-2'-methylpropyl)-2-oxo-5-[3''-(2'''-tetrahydropyranyloxy)-trans-1''-octenyl]-cyclopentane-carboxylic acid ethyl ester Test in analogy to Example 1 from 2.84 g (8 mmols) of (5RS,3'SR)-2-Oxo-5-[3'-(2''-tetrahydropyranyloxy)-trans-1'-octenyl]-cyclopentane-carboxylic acid ethyl ester, 1.12 g (10 mmols) of potassium-tert.-butylate and 3.03 g (12 mmols) of 4-iodo-3-methyl-butyric acid ethyl ester in 17 ml of xylene (15 hours at 115°C). Column chromatography on SiO$_2$ (height of the column 25 cm, diameter of the column 3.2 cm). 2.55 g of pure substance and 170 mg of a slightly impure compound.

$R_F$ = 0.25 (cyclohexane/ether 1:1).

The 4-iodo-3-methyl-butyric acid ethyl ester was prepared as follows:

The 4-Bromo-3-methyl-2-butenic acid methyl ester was saponified with an aqueous-alcoholic sodium hydroxide solution to give the 4-hydroxy-3-methyl-trans-2-butenic acid, and the crude product obtained by acidification was converted into the 3-methyl-butyrolactone by hydrogenation with platinum oxide as a catalyst. By boiling for 6 hours with phosphorous tribromide at 110°C and subsequent ethanolyse the 4-bromo-3-methyl-butyric acid ethyl ester was obtained which was converted into the 4-iodo-3-methyl-butyric acid ethyl ester by boiling with sodium iodide in acetone.

EXAMPLE 25

(5RS,3''SR)-1-(3'-Ethoxycarbonyl-2'-methyl-trans-2'-propenyl)-2-oxo-5-[3''-(2'''-tetrahydropyranyloxy)-trans-1''-octenyl]-cyclopentane-carboxylic acid ethyl ester Test in analogy to Example 1 from 1.83 g (5 mmols) of (5RS,3'SR)-2-Oxo-5-[3'-(2''-tetrahydropyranyloxy)-trans-1'-octenyl]-cyclopentane-carboxylic acid ethyl ester, 616 mg (5.5 mols) of potassium-tert.-butylate and 1.13 g (10 mmols) of 4-bromo-3-methyl-crotonic acid ethyl ester (purified by gas chromatography) in 20 ml of absolute benzene (for 14 hours at room temperature, for 4 hours at 70°C). Column chromatography on 100 g of SiO$_2$ yielded 2.07 g of pure product.

NMR: Signals at 5.7 – 5.4 ppm (multiplet) 4.65 ppm (broad signal) 3.7 ppm (singulet) 2.05 ppm (singulet).

EXAMPLE 26

(5RS,3''SR)-1-(7'-Ethoxycarbonylheptyl)-2-oxo-5-[3''-(2'''-tetrahydropyranyloxy)-trans-1''-octenyl]-cyclopentane-carboxylic acid ethyl ester Test in analogy to 4(e) from (5RS, 3'SR)-2-Oxo-5-[3'-(2''-tetrahydropyranyloxy)-trans-1'-octenyl]-cyclopentane-carboxylic acid ethyl ester and 8-iodo-octanoic acid ethyl ester (5 hours reflux temperature).

$R_F$ = 0.28 (SiO$_2$, cyclohexane/ethyl acetate 85:15).

The 8-iodo-octanoic acid ethyl ester was prepared according to the reactions described in Examples 4(a) to 4(d) from 1,6-dibromo-hexane and malonic acid diethyl ester.

Boiling point$_{0.1}$: 84° – 86°C.

EXAMPLE 27

(5RS,3"SR)-1-(6'-Ethoxycarbonyl-4'-oxahexyl)-2-oxo-5-[3"-(2'''-tetrahydropyranyloxy)-trans-1"-octenyl]-cyclopentane-carboxylic acid ethyl ester a. 3-(3-Hydroxyprop-1-oxy)-propionic acid ethyl ester 0.5 g of NaH was added to 152 g (2 mols) of propanediol-1,3 and when the development of hydrogen was finished, 200 g (2 mols) of acrylic acid ethyl ester were added. The temperature was slowly increased to 35°C. After 4 hours at room temperature the mixture was allowed to stand over night in the refrigerator at 5°C. It was acidified with 1.5 ml. of glacial acetic acid and distributed between methylene chloride and water. The aqueous phase was extracted several times with methylene chloride, the combined organic phases were washed twice with saturated sodium hydroxide solution, dried and evaporated. The residue was fractionated under highly reduced pressure. Boiling point$_{0.4}$: 105°C.

b. 3-(3-bromoprop-1-oxy)-propionic acid ethyl ester 29.8 g (0.11 mol) of phosphor tribromide were added dropwise within 15 minutes, with stirring, exclusion of humidity and cooling with water, to 35.2 g (0.2 mol) of 3-(3-hydroxypropyl-1-oxy)propionic acid ethyl ester in 200 ml of petroleum ether.

Afer 1 hour 5 ml of ethanol were added dropwise, while cooling with ice, and the reaction mixture was distributed between ice water and benzene. The organic phase was washed with saturated NaHCO$_3$-solution, dried, evaporated and distilled off.

Boiling point$_{0.4}$: 80 – 82°C.

c. 3(3-Iodo-prop-1-oxy)-propionic acid ethyl ester

Reaction in analogy to 4(d) from 3-(3-bromopropyl-1-oxy)-propionic acid ethyl ester.

Boiling point$_{0.9}$: 105° – 106°C

NMR: 4.19 ppm (2 prot., quadruplet); 3.84 – 3.40 ppm (4 prot., two triplets); 3.26 ppm (2 prot., triplet); 2.57 ppm (2 prot., triplet); 2.10 ppm (2 prot., sextet); 1.26 ppm (3 prot., triplet).

d. (5RS,3"SR)-1-(6'-Ethoxycarbonyl-4'-oxahexyl)-2-oxo-5-[3"-(2'''-tetrahydropyranyloxy)-trans-1"-octenyl]-cyclopentane-carboxylic acid ethyl ester Test in analogy to 4(e) from (5RS,3'SR)-2-Oxo-5-[3'-(2"-tetrahydropyranyloxy)-trans-1'-octenyl]-cyclopentane-carboxylic acid ethyl ester and 3-(3-iodoprop-1-oxy)-propionic acid ethyl ester (5.5 hours, reflux temperaure).

R$_F$ = 0.52 (cyclohexane/ethyl acetate 1:1) NMR: 5.40 ppm (2 prot., multiplet); 4.63 ppm (1 proton); 4.39 – 3.06 ppm (11 protons); 2.50 – 0.70 ppm (34 protons).

EXAMPLE 28

(5RS,3"SR)-1-(6'-Ethoxycarbonyl-5'-methyl-4'-oxahexyl)-2-oxo-5-[3"-tetrahydropyranyloxy)-trans-1"-octenyl]-cyclopentane-carboxylic acid ethyl ester Test in analogy to Example 1 from 2.2 g (6 mmols) of (5RS,3'SR)-2-Oxo-5-[3'-(2"-tetrahydropyranyloxy)-trans-1'-octenyl]-cyclopentane-carboxylic acid ethyl ester, 900 mg (8 mmols) of potassium-tert.-butylate and 3 g (10 mmols) of 7-iodo-3-methyl-4-oxa-heptanoic acid ethyl ester in 25 ml of toluene (6 hours at 110°C) column chromatography on 120 g of SiO$_2$.

1.57 g of a pure compound and 544 mg of a slightly impure product were obtained.

R$_F$ = 0.4 (cyclohexane/ether 1:1).

The 7-iodo-3-methyl-4-oxaheptanoic acid ethyl ester was obtained in the following manner:

The 3-chloropropanol was added to the crotonic acid ethyl ester in the presence of sodium hydride to obtain the 7-chloro-3-methyl-4-oxaheptanoic acid ethyl ester (boiling point$_1$: 74° – 82°C.). Then the 7-iodo-3-methyl-4-oxaheptanoic acid ethyl ester (boiling point$_{0.05}$: 62° – 65°C) was obtained in acetone with sodium iodide according to Finkelstein.

EXAMPLE 29

(5RS,3"SR)-1-(6'-Methoxycarbonyl-5'-oxahexyl)-2-oxo-5-[3"-(2'''-terahydropyranyloxy)-trans-1"-octenyl]-cyclopentane-carboxylic acid ethyl ester Test in analogy to Example 1 from 735 mg (2 mmols) of (5RS,3'SR)-2-Oxo-5-[3'-(2"-tetrahydropyranyloxy)-trans-1'-octenyl]-cyclopentane-carboxylic acid ethyl ester, 300 mg (2.7 mmols) of potassium-tert.-butylate and 740 mg of 7-iodo-3-oxaheptanoic acid methyl ester in 18 ml toluene (8 hours at 100°C).

R$_F$ = 0.23

| NMR: | |
|---|---|
| 5.5 – 5.7 ppm | 2 clefinical protons |
| 4.65 ppm | 1 proton |
| 4.1 ppm | 2 protons |
| 3.75 ppm | 2 protons |

The 7-iodo-3-oxa-heptanoic acid methyl ester was obtained from 1,4-diiodo-butane and glycolic acid methyl ester in tetrahydrofurane in the presence of sodium hydride.

Boiling point$_{0.1}$: 76° – 82°C.

EXAMPLE 30

(5RS,3"SR)-1-(6"-Carboxy-5'-oxahexyl)-2-hydroxy-5-[3"-hydroxy-trans-1"'-octenyl]-cyclopentane-carboxylic acid ethyl ester 250 mg of (5RS,3"SR)-1-(6'-Ethoxycabonyl-5'-oxahexyl)-2-oxo-5-[3"-(2''''-tetrahydropyranyloxy)-trans-1"'-octenyl]-cyclopentane-carboxylic acid ethyl ester were mixed in 10 ml of methanol at 0°C twice with 125 mg in each case of sodium borohydride, after one hour 1 ml of a 0.5N sodium hydroxide solution was added, and the mixture was stirred for 6 hours at room temperature, then acidifed with 2N hydrochloric acid to a pH value of 1 – 2 and extracted with diethyl ether. After washing with water and drying over sodium sulfate the solvent was distilled off under reduced pressure, and 170 mg of an oily residue were obtained, which was dissolved in 8 ml of ethanol and stired with 4 ml of a 2% oxalic acid for 8 hours at 40°C and for 12 hours at room temperaure. The ethanol was distilled off under reduced pressure and the residue was extracted with ether after mixing with a saturated sodium chloride solution. The ether was washed with water, dried and evaporated. The crude product was chromatographed on silica gel. (Height of the filling: 8 cm, diameter 2 cm). The product was eluated first with 200 ml of cyclohexane/ether 1:1 and then with 200 ml of a cyclohexane/ethyl acetate mixture in the ratio of 1:9 and on the whole 140 fractions were taken off. The fractions 40 to 100 contained 78 mg of the substance desired in pure form.

R$_F$ = 0.11 (cyclohexane/ethyl acetate/glacial acetic acid 40:60:1).

EXAMPLE 31

(5RS,3''SR)-1-(6'-Ethoxycarbonyl-5'-oxo-cis-2'-hexenyl)-2-oxo-5-[3''-(2''-tetrahydropyranyloxy)-trans-1''-octenyl]-cyclopentane-carboxylic acid ethyl ester Test in analogy to Example 1 from 900 mg (2.5 mmols) of (5RS,3'SR)-2-Oxo-5-[3'-(2''-tetrahydropyranyloxy)-trans-1'-octenyl]-cyclopentane-carboxylic acid ethyl ester, 430 mg (3.3 mmols) of potassium-tert.-butylate and 1.1 g (4.6 mmols) of 7-bromo-3-oxa-cis-5-heptenoic acid ethyl ester in 22 ml of toluene (6 hours at 80°C). Chromaography on 70 g of silica gel (Merck 70–230 mesh ASTM), 864 mg of pure substance.

$R_F = 0.25$ (cyclohexane/ether 1:1)

| NMR: 5.4 – 5.8 ppm | 4 olafinical protons |
|---|---|
| 4.65 ppm | 1 proton (proton of the tetrahydropyranyl ether group) |
| 3.9 – 4.2 ppm | multiplet |

The 7-bromo-3-oxa-5-cis-heptenoic acid ethyl ester was prepared in the following manner: cis-butene-diol was alkylated in tetrahydrofurane in the presence of sodium hydroxide with bromacetic acid ethyl ester, the 7-hydroxy-3-oxa-5-cis-heptenoic acid ethyl ester was purified by filtration on silica gel and brominated at –5°C with phosphortribromide in pentane. The crude product was chromatographed on silica gel. The product desired was obtained by eluating with a mixture of cyclohexane/ethyl acetate 85:15.

| NMR: Multiplet 5.7 – 6.0 ppm | Triplet 1.35 ppm |
|---|---|
| Mltiplet 4.0 – 4.4 ppm | |

EXAMPLE 32

(5RS,3''SR)-1-(6'-Carboxy-5'-oxa-cis-2'-hexenyl)-2-hydroxy-5-[3''-hydroxy-trans-1''-octenyl]-cyclopentane-carboxylic acid ethyl ester Test in analogy to Example 30 from (5RS,3''SR)-1-(6-ethoxy-carbonyl-5'-oxa-cis-2'-hexenyl)-2-oxo-5-[3''-(2'''-tetrahydropyranyloxy)-trans-1''-octenyl]-cyclopentane-carboxylicacid ethyl ester.

$R_F = 0.13$ (cyclohexane/ethyl acetate/glacial acetic acid 40:60:1)

EXAMPLE 33

(5RS,3''SR)-1-(6-Methoxycarbonyl-5'-oxa-trans-2'-hexenyl)-2-oxo-5-[3''-(2'''-tetrahydropyranyloxy)-trans-1''-octenyl]-cyclopentane-carboxylic acid ethyl ester Test in analogy to Example 1 from 735 mg (2 mmols) of (5RS,3'SR)-2-oxo-5-[3'-(2''-tetrahydropyranyloxy)-trans-1'-octenyl]-cyclopentane-carboxylic acid ethyl ester, 300 mg (2.7 mmols) of potassium-tert.-butylate and 740 mg (3.1 mols) of 7-bromo-3-oxa-trans-5-heptenoic acid methyl ester in 15 ml of toluene (5 hours at 60°C).

The chromatography on 80 g of $SiO_2$ with cyclohexane/ethyl acetate 9:1 yielded 558 mg of the compound desired.

$R_F = 0.14$ (cyclohexane/ether 1:1).

The 7-bromo-3-oxa-trans-5-heptenoic acid methyl ester was obtained by reaction of glycolic acid methyl ester in tetrahydrofurane with sodium hydride and 1,4-dibromo-trans-2-butene.

Boiling point at 0.1 mm: 72° – 74°C.

EXAMPLE 34

(5RS,3''SR)-2-Hydroxy-1-(6'-methoxycarbonyl-5'-oxa-trans-2'-hexenyl)-5-[3''-(2'''-tetrahydropyranyloxy)-trans-1''-octenyl]-cyclopentane-carboxylic acid ethyl ester Test in analogy to Example 1 from (5RS,3''SR)-1-(6'-methoxy-carbonyl-5'-oxa-trans-2'-hexenyl)-2-oxo-5-[3''-2''''-tetra-hydropyranyloxy)-trans-1''-octenyl]-cyclopentanecarboxylic acid ethyl ether.

$R_F = 0.32$ (cyclohexane/ethyl acetate/glacial acetic acid 60:40:1)

| NMR-spectrum | multiplet | 5.4 – 5.7 | ppm |
|---|---|---|---|
| | '' | 3.65 | ppm |
| | '' | 4 – 4.3 | ppm |
| | singulet | 3.65 | ppm |

EXAMPLE 35

(5RS,3''SR)-1-(6'-Carboxy-5'-oxa-trans-2'-hexenyl)-2-hydroxy-5-[3''-(2''''-tetrahydropyranyloxy)-trans-1'''-octenyl]-cyclopentane-carboxylic acid ethyl ester 500 mg of (5RS,3''SR)-2-Hydroxy-1-(6'-methoxycarbonyl-5'-oxa-trans-2'-hexenyl)-5-[3''-(2''''-tetrahydropyranyloxy)-trans-1''-octenyl]cyclopentane-carboxylic acid ethyl ester were stirred in 15 ml of ethanol and 3 ml of a 2N sodium hydroxide solution for 5 hours at room temperature. The mixture was worked up in analogy to Example 5.

$R_F = 0.27$ (cyclohexane/ethyl acetate/glacial acetic acid 40:60:1).

EXAMPLE 36

(5RS,3''SR)-1-(6'-Carboxy-5'-oxa-trans-2'-hexenyl)-2-hydroxy-5-(3'''-hydroxy-trans-1''-octenyl)-cyclopentane-carboxylic acid ethyl ester 97 mg of (5RS,3''SR)-2-Hydroxy-1-(6'-methoxycarbonyl-5'-oxa-trans-2'-hexenyl)-5-[3''-(2''''-tetrahydropyranyloxy)trans-1''-octenyl]-cyclopentane-carboxylic acid ethyl ester were heated for 2 hours to 50°C in 10 ml of absolute ethanol with 5 mg of p-toluene-sulfonic acid under argon. The crude product was chromatographed on silica gel, as has been described several times. When eluating with a mixture of solvents of cyclohexane/ethyl acetate in the ratio of 8:2, 50 mg of a pure substance were obtained.

$R_F = 0.13$ (cyclohexane/ether 1:1).

In the NMR-spectrum the signal characteristic for the tetrahydropyranyloxy group at 4.65 ppm was missing, furthermore the singulet characteristic for the methyl ester group at 3.65 ppm had disappeared, but a quadruplet appeared at 4.2 ppm (2 H) instead (ethyl ester group).

EXAMPLE 37

(5RS,3''SR)-1-(6'-Carboxy-5'-oxa-trans-2'-hexenyl)-2-hydroxy-5-(3''-hydroxy-trans-1''-octenyl)-cyclopentane-carboxylic acid ethyl ester Test in analogy to Example 30 from 220 mg of (5RS,3''SR)-1-(6'-methoxycarbonyl-5'-oxa-trans-2'-hexenyl)-2-oxo-5-[3''-(2'''-tetrahydropyranyloxy)-trans-1''-octenyl]-cyclopentanecarboxylic acid ethyl ester. 97 mg of pure substance with $R_F = 0.12$ (cyclohexane/ethyl acetate/glacial acetic acid 40:60:1) were obtained.

EXAMPLE 38

(5RS,3''SR)-1-(6'-Methoxycarbonyl-5'-oxa-trans-2'-hexenyl)-5-(3''-hydroxy-trans-1''-octenyl)-2-oxo-cyclopentane-carboxylic acid ethyl ester 300 mg of (5RS,3''SR)-1-(6'-methoxycarbonyl-5'-oxa-trans-2'-hexenyl)-2-oxo-5-[3''-(2'''-tetrahydropyranyloxy)-trans-1''-octenyl]-cyclopentane-carboxylic acid ethyl ester were heated for 1.5 hours to 40°C in 20 ml of absolute methanol with 10 mg of p-toluene-sulfonic acid under argon. After addition of triethyl amine the solvent was distilled off under reduced pressure, the residue was taken up in ether, washed with 0.3N sodium hydroxide solution and water, dried and evaporated. By chromatography on silica gel with cyclohexane/ethyl acetate 7:3 as an eluent, 210 mg of a pure product were obtained.

$R_F = 0.20$ (cyclohexane/ethyl acetate/glacial acetic acid 60:40:1)

In the NMR-spectrum the signal characteristic for the tetrahydropyranyl ether group was missing at 4.65 ppm.

EXAMPLE 39

(5RS,3''SR)-1-(6'-Methoxycarbonyl-5'-oxa-trans-2'-hexenyl)-5-[3''-(3'''-cyclopentylpropylcarbonyloxy)-trans-1''-octenyl]-2-oxocyclopentane-carboxylic acid ethyl ester 107 mg (0.25 mmol) of (5RS,3''SR)-1-(6'-Methoxycarbonyl-5'-oxa-trans-2'-hexenyl)-5-(3''-hydroxy-trans-1''-octenyl)-2-oxocyclopentane-carboxylic acid ethyl ester were dissolved in 3 ml of pyridine and 45 mg (0.25 mmol) of 3-cyclopentylpropionic acid chloride were added at 0°C. Then the mixture was stirred for 1.5 hours at room temperature. The pyridine was distilled off at 30°C under reduced pressure, the residue was mixed with ice and extracted with diethyl ether. After washing, drying and evaporating 170 mg of the crude product remained. 115 mg of pure substance were obtained by chromatography on silica gel and elution with cyclohexane/ethyl acetate 7:3.

$R_F = 0.65$ (cyclohexane/ether 1:1)

EXAMPLE 40

(5RS,3''SR)-1-(6'-Ethoxycarbonyl-5'-oxaheptyl)-2-oxo-5-[3''-(2'''-tetrahydropyranyloxy)-trans-1''-octenyl]-cyclopentane-carboxylic acid ethyl ester Test in analogy to Example 4(e) from (5RS,3'SR)-2-Oxo-5[3'-(2''-tetrahydropyranyloxy)-trans-1'-octenyl]-cyclopentanecarboxylic acid ethyl ester and 7-iodo-2-methyl-3-oxaheptanoic acid ethyl ester (6 hours at 110°C).

$R_F = 0.27$ (cyclohexane/ethyl acetate 85:15)

The 7-iodo-2-methyl-3-oxoheptanoic acid ethyl ester was prepared in the following manner:

The lactic acid ethyl ester and 1,4-dibromo-butane were reacted in THF in the presence of NaH to obtain 7-bromo-2-methyl-3-oxaheptanoic acid ethyl ester and subsequently, the exchange of bromine and iodine was carried out, as described in 4(d).

Boiling point$_{2.3}$: 120° – 123°C.

EXAMPLE 41

(5RS,3''SR)-1-(5'-Ethoxycarbonyl-4'-oxapentyl)-2-oxo-5-[3''-(2'''-tetrahydropyranyloxy)-trans-1''-octenyl]-cyclopentane-carboxylic acid ethyl ester In analogy to 4(e) from (5RS,3'SR)-2-Oxo-5-[3'-(2''-tetrahydropyranyloxy)-trans-1'-octenyl]-cyclopentane-carboxylic acid ethyl ester and 3-iodo-propoxy-acetic acid ethyl ester. NMR: 5.7 – 5.4 ppm (2 prot., multiplet); 4.65 ppm (1 prot., broad singulet), the signal group between 4.4 and 3.8 ppm was superimposed by a sharp singulet at 4.05 ppm (8 protons on the whole), 3.54 ppm (3 protons, multiplet), 3.0 – 0.8 ppm (32 protons, multiplet).

$R_F = 0.33$ (cyclohexane/ethyl acetate 8:2).

The 3-iodo-propoxy-acetic acid ethyl ester was prepared in analogy to Example 4 d) from 3-cloro-propoxy-acetic acid ethyl ester (Suomen Kemistilehti 17 B, 17 (1944), cf. CA 40, 6491 (1946)).

Boiling point$_{0.65}$: 85°C.

EXAMPLE 42

(5RS,3''SR)-1-(4'-Ethoxycarbonyl-3'-oxabutyl)-2-oxo-5-[3''-(2'''-tetrahydropyranyloxy)-trans-1''-octenyl]-cyclopentane-carboxylic acid ethyl ester Test in analogy to 4(e) from (5RS,3'SR)-2-oxo-5-[3'-(2''-tetrahydropyranyloxy)-trans-1'-octenyl]-cyclopentanecarboxylic acid ethyl ester and 2-iodo-ethoxy-acetic acid ethyl ester.

$R_F = 0.30$ (cyclohexane/ethyl acetate 8:2)

The NMR-spectrum was similar to the spectrum indicated in Example 41.

The 2-iodethoxy-acetic acid ethyl ester was synthetized in analogy to Example 4 d) from 2-chloro-ethoxy-acetic acid ethyl ester (Suomen Kemistilehti 17 B, 17 (1944), cf. CA 40, 6491 (1946)).

Boiling point$_{0.3}$: 72° – 75°C.

EXAMPLE 43

(5RS,3''SR)-1-(7'-Methoxycarbonyl-5'-oxa-cis-2'-heptenyl)-2-oxo-5-[3''-(2'''-tetrahydropyranyloxy)-trans-1''-octenyl]-cyclopentane-carboxylic acid ethyl ester Reaction in analogy to Example 1 from 2.2 g (6 mmols) of (5RS,3'SR)-2-oxo-5-[3'-(2''-tetrahydropyranyloxy)-trans-1'-octenyl]-cyclopentane-carboxylic acid ethyl ester, 900 mg (8 mmols) of potassium-tert.-butylate and 2.37 g (10 mmols) of 8-bromo-4-oxa-cis-6-octenoic acid methyl ester in 25 ml of toluene (6 hours; 60°C).

After column chromatography on 120 g of SiO$_2$ 1.73 g of a pure product were obtained, furthermore 0.80 g of a slightly contaminated product.

$R_F = 0.33$ (cyclohexane/ethyl acetate 8:2).

The 8-bromo-4-oxa-Δ6-cis-octenoic acid methyl ester was prepared in the following manner:

The cis-butene-diol was added to the acrylic acid methyl ester in the presence of NaH; the crude 8- hydroxy-4-oxa-cis-6-octenoic acid methyl ester was purified by chromatography on silica gel (elution with ethyl acetate/cyclohexane 1:1) and converted with phosphortribromide in pentane at −5° to −10°C into the crude 8-bromo-4-oxa-cis-6-octenoic acid methyl ester. This ester was chromatographed on silica gel. By elution with cyclohexane/ethyl acetate 95:5 the pure ester was obtained.

| NMR: | multiplet | 5.7 – 6.0 ppm |
|---|---|---|
| | singulet | 3.7 ppm, multiplet 3.7 – 4.2 ppm |
| | triplet | 2.55 ppm |

EXAMPLE 44

(5RS,3'''SR)-1-[2'-(3''-Ethoxycarbonylpropyl)-benzyl]-2-oxo-5-[3'''-(2''''-tetrahydropyranyloxy)-trans-1'''-octenyl]-cyclopentane-carboxylic acid ethyl ester a. Acetic acid-2-(3-chlorpropyl)-benzyl ester 70 g (345 mmols) of 3-(2-Chloromethylphenyl)-propyl chloride (JACS 75, 2053 (1953)) and 50 g (0.61 mmol) of sodium acetate were heated to the boiling point while stirring in 250 ml of glacial acetic acid. It resulted from the thin layer chromatography that the reaction was finished after 4½ hours. After cooling about 700 ml of water were added and the product was extracted with benzene. The organic phase was washed with water, dried and distilled off after evaporation of the solvent.

Boiling point$_{0.1}$: 101°C.

b. Acetic acid-2-(3-cyanopropyl)-benzyl ester

With exclusion of humidity 12.5 g (0.25 mol) of dry NaCN were heated in 65 ml of anhydrous DMSO to 90°C and at this temperature 44.8 g (0.2 mol) of acetic acid-2-(3-chloropropyl)-benzyl ester were added dropwise. Then the mixture was heated for 50 minutes to 120°C and distributed after cooling between water and ether. The aqueous phase was extracted three times with ether, the organic phase was washed three times with a saturated sodium chloride solution, dried and concentrated under reduced pressure. The product boiled at 128°C/0.2 mm mercury.

c. 4-(2-Bromomethylphenyl)-butyric acid ethyl ester

A solution of 21.4 g of 4-(2-acetoxymethylphenyl)-butyronitrile in 90 ml of absolute ethanol was saturated with a dry hydrogen bromide while cooling with ice and with exclusion of humidity. The mixture was allowed to stand over night at 0° – 5°C, the hydrobromide of the iminoether being precipitated. The solvent was evaporated under reduced pressure, and the residue was added, while stirring, to a mixture of water, ether and NaHCO$_3$ in excess. The ether layer was washed with a saturated NaHCO$_3$-solution, dried and evaporated. The yellowish oil consisting for the most part of the free imino ether, was chromatographed on 100 g of SiO$_2$ with benzene saturated with water as eluent, whereby the imino ether was hydrolized to the ethyl ester.

Colorless oil, R$_F$ = 0.39 (benzene)

| C$_{13}$H$_{17}$BrO$_2$ | C calc. | 54,78 % (found: 54,8 %) |
|---|---|---|
| | H calc. | 6,01 % (found: 6,0 %) |
| | Br calc. | 28,01 % (found: 28,5%) |

NMR: 7.3 ppm (4 prot.), 4.58 ppm (2 prot., singulet), 4.19 ppm (2 prot., quadruplet), 3.0 – 1.6 ppm (6 prot., multiplet), 1.26 ppm (3 prot., triplet).

d. (5RS,3'''SR)-1-[2'-(3''-Ethoxycarbonylpropyl)-benzyl]-2-oxo-5-[3'''-(2''''-tetrahydropyranyloxy)-trans-1'''-octenyl]-cyclopentane-carboxylic acid ethyl ester Reaction in analogy to 4(e) from (5RS,3'SR)-2-Oxo-5-[3'-(2''-tetrahydropyranyloxy)-trans-1'-octenyl]-cyclopentane-carboxylic acid ethyl ester and 4-(2-bromo-methylphenyl)-butyric acid ethyl ester, but the reaction took place by merely heating to 50°C during 2 hours.

R$_F$ = 0.58 (cyclohexane/ethyl acetate 1:1)

NMR: 7.11 ppm (4 prot., multiplet), 5.53 ppm (2 prot., multiplet), 4.66 ppm (1 prot.), 4.5 – 3.5 ppm (7 prot., multiplet), 3.34 ppm (2 prot., singulet), 3.10 – 0.70 ppm (34 protons).

Example 45

(5RS,3'''SR)-1-[2'-(3''-Carboxypropyl)-benzyl]-2-hydroxy-5-[3'''-(2''''-tetrahydropyranyloxy)-trans-1'''-octenyl]-cyclopentane-carboxylic acid ethyl ester Test in analogy to Example 5 from (5RS,3'''SR)-1-[2'-(3''-ethoxycarbonylpropyl)-benzyl]-2-oxo-5-[3'''-(2''''-tetrahydropyranyloxy)-trans-1'''-octenyl]-cyclopentane-carboxylic acid ethyl ester.

R$_F$ = 0.28 (cyclohexane/ethyl acetate/glacial acetic acid 40:60:1)

EXAMPLE 46

(5RS,3'''SR)-1-[2'-(3''-Carboxypropyl)-benzyl]-2-hydroxy-5-[3'''-hydroxy-trans-1'''-octenyl]-cyclopentane-carboxylic acid ethyl ester Test in analogy to Example 6 from (5RS,3'''SR)-1-[2'-(3''-carboxypropyl)-benzyl]-2-hydroxy-5-]3'''-(2''''-tetrahydropyranyloxy)-trans-1'''-octenyl]-cyclopentane-carboxylic acid ethyl ester.

R$_F$ = 0.19 (cyclohexane/ethyl acetate/glacial acetic acid 40:60:1)

EXAMPLE 47

(5RS,3'''SR)-1-[3'-(4''-Ethoxycarbonylphenyl)-propyl]-2-oxo-5-[3'''-(2''''-tetrahydropyranyloxy)-trans-1'''-octenyl]-cyclopentane-carboxylic acid ethyl ester a. 4-(3-Bromo-propyl)-benzoic acid ethyl ester 100 g 4-(3-Bromo-propyl)-benzoic acid (JACS 65, 2281 (1943)), 400 ml of toluene and 80 ml of thionyl chloride were refluxed for 4 hours. The solvent and the thionyl chloride in excess were removed under reduced pressure and after addition of 400 ml of absolute ethanol to the residue the mixture was heated for 1 hour to the boiling point. It was evaporated under reduced pressure, the residue was taken up in benzene and washed neutral with a saturated NaHCO$_3$-solution. The organic phase was distilled off after drying with MgSO$_4$.

Boiling point$_{0.1}$: 105° – 107°C.

b. 4-(3-Iodopropyl)-benzoic acid ethyl ester

Test in analogy to 4(d) from 4-(3-bromopropyl)-benzoic acid ethyl ester.

Boiling point$_{0.15}$: 117° – 119°C.

c. (5RS,3'''SR)-1-[3'-4''-Ethoxycarbonylpentyl)-propyl]-2-oxo-5-[3'''-(2''''-tetrahydropyranyloxy)-trans-1'''-octenyl]-cyclopentane-carboxylic acid ethyl ester Test in analogy ot 4 (e) from (5RS,3'SR)-2-oxo-5-[3'-(2''-tetrahydropyranyloxy)-trans-1'-octenyl]-cyclopentane-carboxylic acid ethyl ester and 4-(3-iodo-propyl)-benzoic acid ethyl ester (6 hours, 110°C).

$R_F$ = 0.59 (cyclohexane/ethyl acetate 1:1)

NMR: 7.61 ppm (4 protons, $A_2B_2$-Typ), 5.67 – 5.34 ppm (2 prot., multiplet), 4.65 ppm (1 proton), 4.50 – 3.30 ppm (7 protons), 3.30 – 0.70 ppm (34 protons).

EXAMPLE 48

(5RS,3'''SR)-1-[4'-(2''-Ethoxycarbonylethyl)-benzyl]-2-oxo-5-[3''''-(2'''''-tetrahydropyranyloxy)-trans-1'''octenyl]-cyclopentane-carboxylic acid ethyl ester a. 4-Hydroxymethyl-hydrocinnamic acid 30 g (0.15 mol) of 4-chloromethyl-hydrocinnamic acid (J.Org. Chem. 26, 148 (1961) in 200 ml of water were neutralized with a 10% sodium hydroxide solution against phenol phthaline. 10% of NaOH (on the whole about 60 ml) were added dropwise, while stirring at reflux temperature, to the solution obtained in the same measure as it was consumed. When the reaction was finished, the mixture was saturated with sodium chloride, acidifed with concentrated hydrochloric acid, the product precipitated was suction-filtered and washed with water. Melting point: 124° – 126°C.

b. 4-Bromomethylhydrocinnamic acid ethyl ester 18 g (0.1 mol) of 4-hydroxymethyl-hydrocinnamic acid and 40.6 g (0.15 mol) of phosphortribromide in 50 ml of chloroform were heated for 2 hours to 50°C. After cooling, 50 ml of absolute ethanol were added dropwise to the reaction mixture and it was allowed to stand over night. The solvent was removed under reduced pressure, and the residue was distilled off under highly reduced pressure. The product solidified in the recipient.

Boiling point 0.15: 111° – 115°C.

Melting point: 131.5° – 132°C.

c. (5RS,3'''SR)-1-[4'-(2''-Ethoxycarbonylethyl)-benzyl]-2-oxo-5-[3''''-(2'''''-tetrahydropyranyloxy)-trans-1'''-octenyl]-cyclopentane-carboxylic acid ethyl ester Reaction in analogy to 4 (e) from (5RS,3'SR)-2-oxo-5-[3'-(2''-tetrahydropyranyloxy)-trans-1'-octenyl]-cyclopentane-carboxylic acid ethyl ester and 4-bromomethyl-hydrocinnamic acid ethyl ester. To carry out the alkylation, it was sufficient to heat the mixture in this case for 1 hour to 50°C.

$R_F$ = 0.42 ($Al_2O_3$, cyclohexane/ether 1:1) = 0.49 ($SiO_2$, cyclohexane/ethyl acetate 6:4).

EXAMPLE 49

(5RS,3''SR)-1-(4'-Ethoxycarbonylbenzyl)-2-oxo-5-[3''-(2'''-tetrahydropyranyloxy)-trans-1''-octenyl]-cyclopentane-carboxylic acid ethyl ester Reaction in analogy to 4 (e) from (5RS, 3'SR)-2-oxo-5-[3'-(2''-tetrahydropyranyloxy)-trans-1'-octenyl]-cyclopentane-carboxylic acid ethyl ester and 4-bromomethyl-benzoic acid ethyl ester (Soc. 1928, 2581, see also JACS 62, 1180 (1940)). In this case the reaction was already finished in 2 hours at 50°C. $R_F$ = 0.46 ($Al_2O_3$, cyclohexane/ether 1:1) = 0.53 ($SiO_2$, cyclohexane/ethyl acetate 1:1)

NMR: 7.54 ppm (4 prot., $A_2B_2$-type); 5.52 ppm (2 prot., multiplet); 4.62 ppm (1 prot., broad singulet); 4.5 – 3.7 ppm (7 prot.); 3.28 ppm (2 prot., doublet); 2.8 – 0.8 ppm (28 protons).

EXAMPLE 50

(5RS,3''''SR)-1-[2'-(4''-Ethoxycarbonylphenoxy)-ethyl]-2-oxo-5-[3'''-(2''''-tetrahydropyranyloxy)-trans-1'''-octenyl]-cyclopentane-carboxylic acid ethyl ester a. 4-(2-Bromo-ethoxy)-benzoic acid ethyl ester A solution of 68 g of 4-(2-bromoethoxy)-benzonitrile in 500 ml of absolute ether and 50 ml of absolute ethanol was saturated with dry hydrogen chloride while cooling with ice. After standing for 3 days in the refrigerator the precipitated hydrochloride of the imino ether was suction-filtered, suspended in water/ether and $NaHCO_3$ was added while stirring until the development of $CO_2$ was finished. The organic phase was dried with $MgSO_4$ and the solvent was evaporated under reduced pressure. 100 ml of absolute ethanol and 3 ml of concentrated sulfuric acid were added to the residue and the whole was heated to the boiling point for 1 hour.

After cooling the solvent was removed and the residue was distributed between benzene and saturated $NaHCO_3$-solution. The organic phase was evaporated after drying, whereby the 3-carbethoxy-phenoxyethyl bromide was obtained as a light yellow oil. It was immediately further reacted.

b. 4-(2-Iodethoxy)-benzoic acid ethyl ester

Reaction in analogy to 4 (d) from 4-(2-bromethoxy)-benzoic acid ethyl ester.

Melting point: 57°– 58°C (from petroleum ether).

NMR: 7.47 ppm (4 prot., $A_2B_2$); 4.6 – 4.15 ppm (4 prot., quadruplet and triplet); 3.42 ppm (2 prot., triplet); 1.37 ppm (3 prot., triplet).

c. (5RS,3'''SR)-1-[2'-(4''-Ethoxycarbonylphenoxy)-ethyl]-2-oxo-5-[3''''-(2'''''-tetrahydropyranyloxy)-trans-1'''-octenyl]-cyclopentane-carboxylic acid ethyl ester Test in analogy to 4 (e) from (5RS,3'RS)-2-oxo-5-[3'-(2''-tetrahydropyranyloxy)-trans-1'-octenyl]-cyclopentane-carboxylic acid ethyl ester and 4-(2-iodethoxy)-benzoic acid ethyl ester (5 hours, 110°C).

$R_F$ = 0.48 (cyclohexane/ethyl acetate 6:4).

EXAMPLE 51

(5RS,3''SR)-1-(5'-Ethoxycarbonylfurfuryl)-2-oxo-5-[3'''-(2''''-tetrahydropyranyloxy)-trans-1''-octenyl]-cyclopentane-carboxylic acid ethyl ester Test in analogy to Example 1 from 2.94 g (8 mmols) of (5RS,3'SR)-2-oxo-5-[3'-(2''-tetrahydropyranyloxy)-trans-1'-octenyl]-cyclopentane-carboxylic acid ethyl ester, 1.12 g (10 mmols) of potassium-tert.-butylate and 2.81 g (12 mmols) of 5-bromomethyl-2-furane-carboxylic acid ethyl ester in 35 ml of xylene (3 hours at 100°C). After chromatography on $SiO_2$ (column 25 × 3.5 cm) 2.5 g of a pure product and 650 mg of a slightly contaminated product were obtained.

NMR: 7.05 ppm (doublet); 6.0 ppm (doublet); 5.50 ppm (multiplet); 4.6 – 4.0 ppm (multiplet); 3.30 ppm (singulet).

EXAMPLE 52

(5RS,3''SR)-1-(6'-Ethoxycarbonyl-3'-methylhexyl)-2-oxo-5-(3''-hydroxy-trans-1''-octenyl)-cyclopentane-carboxylic acid ethyl ester 100 mg of o-toluene-sulfonic acid were added to 1.12 g of (5RS,3''SR)-1-(6'-ethoxycarbonyl-3'-methylhexyl)-2-oxo-5-k[3''-(2''''-tetrahydropyranyloxy)-trans-1'''-octenyl]-cyclopentane-carboxylic acid ethyl ester in 50 ml of absolute ethanol, and the mixture was stirred for 5 hours at 40°C. The mixture was adjusted to an alkaline range with 0.2 ml of dry triethyl amine and the solvent was removed at a bath temperature of 20°C under reduced pressure. The residue was distributed between ether and the saturated sodium hydrogen-carbonate solution, the organic phase was washed once more with water and dried. After evaporating an oil was obtained which was purified by chromatography on 40 g of $SiO_2$ (eluent chloroform).

$R_4 = 0.12$ ($CHCl_3$)

NMR: 5.62 ppm (2 H, multiplet);

4.13 ppm (5 H, quadruplet superimposed by broad multiplet).

EXAMPLE 53

(5RS,3''SR)-1-(6'-Ethoxycarbonyl-3'-methylhexyl)-2-oxo-5-(3''-acetoxy-trans-1'''-octenyl)-cyclopentane-carboxylic acid ethyl ester 1 ml of acetanhydride was introduced, while stirring, to 2 ml of dry pyridine, under argon and while cooling with ice. A solution of 300 mg of (5RS,3''SR)-1-(6-ethoxycarbonyl-3'-methylhexyl)-2-oxo-5-(3''-hydroxy-trans-1'''-octenyl)-cyclopentane-carboxylic acid ethyl ester in 1 ml of pyridine was added to the mixture, which was stirred for 15 hours at room temperature. 10 ml of ice water were added, the pH-value was adjusted to 5 – 6 and the product was extracted with ether. The ether phase was washed with water, dried with $MgSO_4$ and evaporated. The residue was purified on 40 g of $SiO_2$ with cyclohexane/ethyl acetate/glacial acetic acid 90:10:1 as an eluent.

$R_F = 0.50$ (cyclohexane/ethyl acetate/glacial acetic acid 90:10:1)

NMR: 5.62 ppm (2 H, multiplet); 5.25 ppm (1 H, multiplet); 4.15 ppm (4 H, quadruplet); 2.06 ppm (3 H, singulet).

EXAMPLE 54

(5RS,3''SR)-1-(6'-Ethoxycarbonyl-4'-methylhexyl)-2-oxo-5-(3''-hydroxy-trans-1'''-octenyl)-cyclopentane-carboxylic acid ethyl ester Test in analogy to Example 52 from (5RS,3''SR)-1-(6'-ethoxy-carbonyl-4'-methylhexyl)-2-oxo-5-[3''-(2''''-tetrahydropyranyloxy)-trans-1'''-octenyl]-cyclopentane-carboxylic acid ethyl ester.

$R_F = 0.38$ (cyclohexane/ethyl acetate/glacial acetic acid 60:40:1).

The NMR-spectrum was practically identical to the spectrum described in Example 52.

EXAMPLE 55

(5RS,3''SR)-1-(6'-Ethoxycarbonyl-5'-methylhexyl)-2-oxo-5-(3''-hydroxy-trans-1'''-octenyl)-cyclopentane-carboxylic acid ethyl ester Test in analogy to Example 52 from (5RS,3''SR)-1-(6-ethoxycabonyl-5'-methylhexyl)-2-oxo-5-[3''-(2''''-tetrahydropyranyloxy)-trans-1'''-octenyl]-cyclopentane-carboxylic acid ethyl ester.

$R_F = 0.25$ (chloroform/ethyl acetate 9:1).

The NMR-spectrum of this compound was nearly identical to the spectrum described in Example 52.

EXAMPLE 56

(5RS,3''SR)-1-(6'-Ethoxy-2'-methylhexyl-2-oxo-5-[3''-(2''''-tetrahydropyranyloxy)-trans-1'''-octenyl]-cyclopentane-carboxylic acid ethyl ester Test in analogy to Example 4 from (5RS,3'SR)-2-oxo-5-[3'-(2''-tetrahydropyranyloxy)-trans-1'-octenyl]-cyclopentane-carboxylic acid ethyl ester and 7-iodo-6-methylheptane-carboxylic acid ethyl ester.

$R_F = 0.48$ (cyclohexane/ethyl acetate 7:3)

NMR: 5.4 – 5.7 ppm (2 H, multiplet); 4.68 ppm (1 H, broad singulet).

The 7-Iodo-6-methylheptane-carboxylic acid ethyl ester was prepared in the following manner:

6-Bromo-2-methylhexanoic acid was prepared from methyl-malonic acid and 1,4-dibromobutane in analogy to Example 4(a) and 4(b). The reduction with diborane yielded 6-bromo-2-methylhexanol (boiling point$_{0.8}$: 75° – 78°C) and the following reaction with NaCN yielded 6-methyl-7-hydroxyheptanoic acid nitrile (boiling point$_{0.3}$: 92° – 97°C).

By addition of phosphortribromide and after heating with aqueous hydrogen bromide the 7-bromo-6-methyl-heptanoic acid was obtained which was esterified with ethanol in analogy to Example 4(c) and then reacted with sodium iodide in analogy to Example 4(d) to 7-iodo-6-methylheptanoic acid ethyl ester (boiling point$_{0.4}$: 85° – 90°C).

EXAMPLE 57

(5RS,3''SR)-1-(6'-Ethoxycarbonyl-2'-methylhexyl)-2-oxo-5-(3''-hydroxy-trans-1'''-octenyl)-cyclopentane-carboxylic acid ethyl ester Test in analogy to Example 52 from (5RS,3''SR)-1-(6'-ethoxy-2'-methylhexyl)-2-oxo-5-[3''-(2''''-tetrahydropyranyloxy)-trans-1'''-octenyl]-cyclopentane-carboxylic acid ethyl ester.

$R_F = 0.36$ (cyclohexane/ethyl acetate/glacial acetic acid 60:40:1).

The NMR-spectrum was nearly identical to the spectrum described in Example 52.

EXAMPLE 58

(5RS,3''SR)-1-(6'-Ethoxycarbonyl-3'-ethylhexyl)-2-oxo-5-[3''-(2''''-tetrahydropyranyloxy)-trans-1''-octenyl]-cyclopentane-carboxylic acid ethyl ester Reaction in analogy to Example 4 from (5RS,3'SR)-2-oxo-5-[3'-(2''-tetrahydropyranyloxy)-trans-1-octenyl]-cyclopentane-carboxylic acid ethyl ester and 7-iodo-5-ethylheptanoic acid ethyl ester.

$R_F$: 0.62 (cyclohexane/ethyl acetate/glacial acetic acid 60:40:1).

NMR-spectrum: 5.4 – 5.7 ppm (2 H, multiplet); 4.65 ppm (1 H, broad singulet); 4.12 ppm (quadruplet, superimposed by multiplet of 3.3 – 4.2 ppm).

The 7-iodo-5-ethylheptane-carboxylic acid ethyl ester was prepared from malonic acid diethyl ester and 1,5-dibromo-3-ethylpentane in analogy to the reactions described in Example 4(a) to 4(d) (boiling point$_{0.25}$: 94° – 96°C).

EXAMPLE 59

(5RS,3''SR)-1-(6'-Ethoxycarbonyl-3'-ethylhexyl)-2-oxo-5-(3''-hydroxy-trans-1''-octenyl)-cyclopentane-carboxylic acid ethyl ester Reaction in analogy to Example 52 from (5RS,3''SR)-1-(6'-ethoxy-carbonyl-3'-ethylhexyl)-2-oxo-5-[3''-(2'''-tetrahydropyranyloxy)-trans-1''-octenyl]-cyclopentane-carboxylic acid ethyl ester.

$R_F = 0.36$ (cyclohexane/ethyl acetate/glacial acetic acid 60:40:1).

The NMR-spectrum of this compound was nearly identical to the spectrum described in Example 52.

EXAMPLE 60

(5RS,3''SR)-1-(6'-Ethoxycarbonyl-2'-methyl-2'-hexenyl)-2-oxo-5-[3''-(2'''-tetrahydropyranyloxy)-trans-1''-octenyl]-cyclopentane-carboxylic acid ethyl ester Reaction in analogy to Example 33 from (5RS,3'SR)-2-oxo-5-[3'-(2''-tetrahydropyranyloxy)-trans-1-octenyl]-cyclo-pentane-carboxylic acid ethyl ester and 7-bromo-6-methyl-5-heptanoic acid ethyl ester.

$R_F = 0.45$ (cyclohexane/ethyl ester 7:3)

NMR: 5.0 – 5.6 ppm (3 olef. H, multiplet).

The 7-bromo-6-methyl-5-heptenoic acid ethyl ester was prepared in the following manner:

The tetrahydropyranyl ether of the hydroxy-acetone resulted in 6-methyl-7-tetrahydropyranyloxy-5-heptenoic acid when reacting it with the ylide of the 4-carboxybutyl-triphenyl-phosphonium bromide. After hydrolisis of the THP protective group the 7-bromo-6-methyl-5-heptenoic acid bromide was obtained with phosphor tribromide which was treated in situ with ethanol and provided the desired 7-bromo-6-methyl-5-heptenoic acid ethyl ester (boiling point$_{0.1}$: 92° – 94°C).

EXAMPLE 61

(5RS,3''SR)-1-(6'-Ethoxycarbonyl-2'-methyl-2'-hexenyl)-2-oxo-5-(3''-hydroxy-trans-1''-octenyl)-cyclopentane-carboxylic acid ethyl ester Reaction in analogy to Example 52 from (5RS,3''SR)-1-(6'-ethoxycarbonyl-2'-methyl-2'-hexenyl)-2-oxo-5-[3''-(2'''-tetrahydropyranyl)-trans-1''-octenyl]-cyclopentane-carboxylic acid ethyl ester.

NMR: 5.1 – 5.6 ppm (3 H, multiplet); 3.8 – 4.3 ppm (quadruplet superimposed by multiplet).

We claim:
1. A cyclopentane compound of the formula

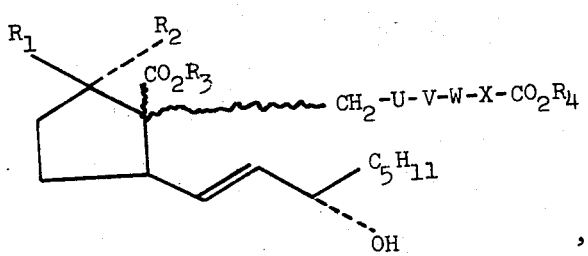

wherein $R_1$ and $R_2$, taken alone, are different and each is hydrogen or hydroxy; $R_1$ and $R_2$, taken together, are oxygen; $R_3$ is alkyl having 1 to 5 carbon atoms; $R_4$ is hydrogen, alkyl having 1 to 5 carbon atoms, or a physiologically tolerable monovalent or polyvalent cation; U is —$(CH_2)_m$—, where $m$ is an integer from 1 to 5; V is a simple bond or

where $R_6$ and $R_7$ are the same or different and are hydrogen or alkyl having 1 to 5 carbon atoms; W is a simple bond or

where $R_8$ and $R_9$ are the same or different and are hydrogen or alkyl having 1 to 5 carbon atoms; and X is —$(CH_2)_m$—, where $m$ is an integer from 0 to 5.

2. A compound as in claim 1 wherein $R_1$ and $R_2$, taken together, are oxygen.

3. A compound as in claim 1 wherein U is —$(CH_2)_m$— and $m$ is an integer from 1 to 3.

4. A compound as in claim 1 which is

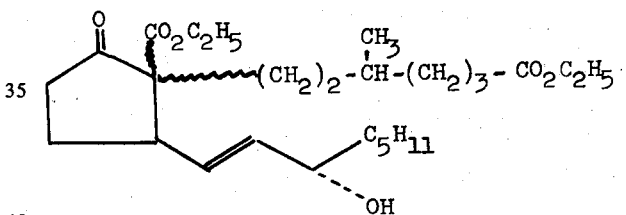

5. A compound as in claim 1 which is

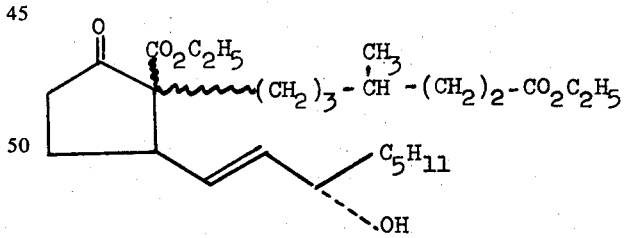

6. A compound as in claim 1 which is

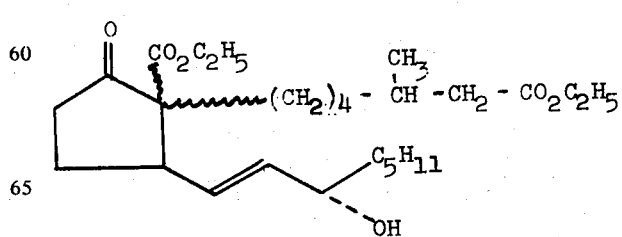

7. A compound as in claim 1 which is
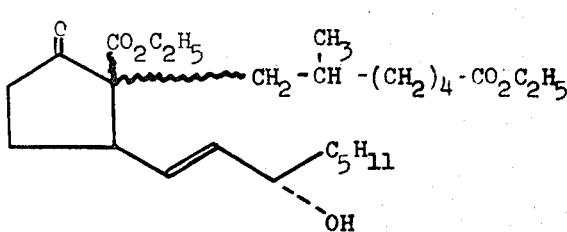
8. A compound as in claim 1 which is
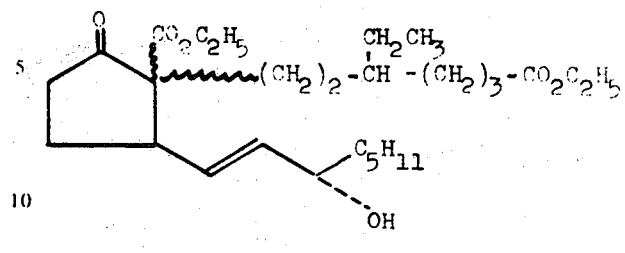
* * * * *